(12) United States Patent
Simard et al.

(10) Patent No.: US 6,260,715 B1
(45) Date of Patent: Jul. 17, 2001

(54) MEANS FOR THE BIOLOGICAL PURIFICATION OF A BIOLOGICAL FLUID

(75) Inventors: Laurent Simard, Saint Genis Laval; Michel Thomas, Serezin du Rhône; Gérard Quash, Francheville; Nicolas Moachon, Craponne, all of (FR)

(73) Assignee: Hospal Industrie (FR)

( * ) Notice: Subject to any disclaimer, the term of this patent is extended or adjusted under 35 U.S.C. 154(b) by 0 days.

(21) Appl. No.: 09/142,607

(22) PCT Filed: Jan. 14, 1998

(86) PCT No.: PCT/FR98/00066

§ 371 Date: Feb. 24, 1999

§ 102(e) Date: Feb. 24, 1999

(87) PCT Pub. No.: WO98/30905

PCT Pub. Date: Jul. 16, 1998

(30) Foreign Application Priority Data

Jan. 14, 1997 (FR) .................................................. 97 00298

(51) Int. Cl.$^7$ .................................................. B01D 69/10
(52) U.S. Cl. .................... 210/490; 210/500.43; 427/245; 422/55; 422/101
(58) Field of Search .................................... 210/645, 650, 210/651, 500.37, 500.38, 500.39, 500.41, 500.43, 490, 638; 422/55, 101; 521/27, 31–33; 525/329.7, 329.8, 329.9, 330.1, 54.2, 54.21, 54.23, 54.24, 54.26, 54.31, 54.32; 424/488; 427/245, 246

(56) References Cited

U.S. PATENT DOCUMENTS

| | | | |
|---|---|---|---|
| 4,545,910 | * 10/1985 | Marze ................................... | 210/651 |
| 4,749,619 | * 6/1988 | Angleraud ........................ | 210/500.43 |
| 5,145,583 | * 9/1992 | Angleraud et al. ............. | 210/500.43 |
| 5,236,592 | * 8/1993 | Dejardin et al. ................ | 210/500.43 |
| 5,240,994 | * 8/1993 | Brink et al. . | |
| 5,401,784 | * 3/1995 | Boillot et al. ........................... | 521/27 |
| 5,417,969 | * 5/1995 | Hsu et al. . | |
| 5,626,760 | * 5/1997 | Pouochilin ...................... | 210/500.43 |
| 6,045,694 | * 4/2000 | Wang et al. .................... | 210/500.37 |

FOREIGN PATENT DOCUMENTS

| | | | |
|---|---|---|---|
| 294905 | * 12/1988 | (EP) . | |
| 312135 | * 4/1989 | (EP) . | |
| 351314 | * 1/1990 | (EP) . | |
| 2197720 | * 5/1988 | (GB) . | |

* cited by examiner

*Primary Examiner*—Joseph W. Drodge
(74) *Attorney, Agent, or Firm*—Finnegan, Henderson, Farabow, Garrett & Dunner

(57) ABSTRACT

A module for extracorporeal purification of a biological fluid includes at least one support or wall defining a compartment which is delimited by an ionic functionalized support or wall, the surface of which is bonded by ionic bonds to a first molecule or macromolecule which exhibits free amine groups to which are covalently bonded a second molecule or macromolecule which exhibits free carboxylic groups which can directly or indirectly form amide, ester or thioester bonds. The invention also includes methods of producing such module.

33 Claims, 19 Drawing Sheets

↓ succinic anhydride

↓ EDC

[$^{14}$C] Glycine

MEANS FOR THE BIOLOGICAL PURIFICATION OF A BIOLOGICAL FLUID

This application is a 371 of PCT/FR98/00066.

The present invention relates to membranes for biological purification of a biological fluid.

The terms purification or biological purification used here means the process of partial or complete elimination of an endogenous or heterologous molecule or macromolecule present in the biological fluid, the complete or partial elimination of which is desired; this molecule or macromolecule can be in a soluble isolated state or it can be complexed with other substances.

The present invention also relates to a multipurpose device for purification of a biological fluid. The device is constituted by a functionalized support which is hemocompatible when used in an extracorporeal circuit for treating blood. The particular feature of the device is that it can covalently bind any type of ligand which can be used to modify the activity or composition of a biological fluid.

The invention also relates to a process for producing and using a support either alone or integrated in a kit for extemporaneous preparation of a support which can carry a specific ligand.

Biocompatible semi-permeable membranes have been developed for dialysis of patients with kidney failure. Such supports can be in the form of flat membranes or hollow fibres. A number of membranes based on synthetic polymers or based on modified cellulose have been developed for users by manufacturers. The polymers used are rarely homopolymers, and no membrane has been exclusively constituted by polyacrylonitrile.

As an example, the PAN membrane from Asahi is constituted by a copolymer of acrylonitrile, methyl methacrylate and acrylic acid; that membrane has an asymmetric microporous structure formed by a dense layer in contact with the blood and a spongy wall on the dialysate side. The SPAN membrane from ENKA is also an asymmetric microporous membrane based on acrylonitrile, sodium methallyl sulphonate and methyl methacrylate.

The AN69 membrane produced and sold by HOSPAL (Meyzieu, France) is based on a copolymer of acrylonitrile and sodium methallyl sulphonate. That membrane is known for its transfer and biocompatibility properties. The number of anionic sites (from the sodium methallyl sulphonate co-monomer) of polymer AN69 is 600 mEq/kg. That of the membrane is about 180 Eq/kg (polymer content approximately 30%).

Other polymers, in particular polysulphone polymers, also have an asymmetric microporous structure; they are fundamentally hydrophobic and must be mixed with hydrophilic components such as polyvinylpyrrolidone to be able to provide dialysis membranes with sufficient diffusive properties.

Symmetrical hydrophilic supports, whether in the form of hollow fibres or of flat membranes depending on the desired usage, also have functional advantages regarding their biocompatibility in that they are low complement activators, they are non thrombogenic and they have a large diffusion capacity.

In general, any biocompatible anionic polymer such as acrylonitrile copolymers can provide supports which are functionalisable using the processes of the invention.

The present invention concerns two types of biological purification: firstly, non specific dialysis and/or hemofiltration type biological purification routinely used for renal dialysis; secondly, biological purification in which an undesirable molecule or macromolecule is eliminated from a biological fluid and by specific interaction of the molecule or macromolecules to be eliminated with one or more ligands covalently coupled to hydrophilic supports.

Dialysis and Hemofiltration

Apparatus for treating blood by extracorporeal circulation are used in a variety of medical or paramedical applications such as: treatment of kidney failure by dialysis or hemofiltration, plasmapheresis and apheresis for therapeutic and non therapeutic ends, blood oxygenation, immuno-purification, etc.

All of the materials used in the manufacture of such apparatus are selected so as to be as biocompatible as possible so that reactions (in particular coagulation) which occur when blood comes into contact with a foreign material do not occur or only occur at relatively benign levels.

Bulk or surface treatment of the materials which come into contact with blood can be treated to improve biocompatibility. Known treatments are carried out either during preparation of the solutions of polymers used to produce a particular part of the apparatus (bulk treatment) or after the different parts of the apparatus have been assembled and before sterilisation of the apparatus, or extemporaneously just before using the apparatus.

One problem which is particularly difficult to resolve occurs when the biocompatibility of the active element of an apparatus is to be improved (for example a dialysis membrane) while satisfying the following conditions:

1) The choice of substance used for the treatment and the treatment conditions must have the result of modifying a known active element, that modification improving the biocompatibility of the active element while preserving all of the known qualities (for example, for a dialysis/hemofiltration membrane: diffusive and convective transfer performances, adsorption capacity of undesirable substances, etc.);
2) Sterilization of the apparatus must not influence the treatment;
3) The treatment must not require particular processing by the user.

More specifically, the inventors propose a process for producing an apparatus which satisfies the above conditions and in which before treatment, the active element carries negative charges on its surface. When blood comes into contact with a negatively charged surface, it forms the seat of a biological phenomenon known as contact phase activation which manifests itself by the generation of active substances, kallikrein and factor XIIa, from inactive substances, prekallikrein and factor XII.

Phase contact activation in itself is benign, but when it occurs simultaneously with certain aggravating factors (the patient taking ACE (angiotensin converting enzyme) inhibitor type antihypertensive drugs, dilution of blood entering an apparatus filled with saline solution, with concomitant pH reduction), it appears to be the origin of undesirable reactions known as anaphylactoids which manifest themselves a few minutes after the start of the treatment in a variety of symptoms, among them a general sensation of heat, engorgement of fingers, lips or tongue, breathlessness, nausea, laryngeal oedema. Anaphylactoid reactions are not exclusively linked to the use of medical apparatus in which the blood compartment has a negatively charged internal surface. Such reactions have been observed with exchangers with membranes of different chemical compositions, both during first use, and after a number of uses when the exchangers, instead of being discarded after a single use, are re-used a number of times and are recycled after each use. An example of an exchanger in which first use is accompanied by an undesirable reaction is a dialyser with a polymethylmethacrylate and polyacrylonitrile membrane. Reactions associated with re-use of dialysers with a cellulose acetate and polysulphone membrane have been well documented (see Anaphylactoid Reactions Associated with Re-use of Hollow-fiber Hemodialyzers and ACE inhibitors in Kidney International, vol. 42 (1992), ppl 1232–1237).

Specific Biological Purification

A number of developments have been made as regards covalent binding of macromolecules to solid supports, more particularly developments intended to increase the specific degree of binding and to reduce the non specific degree of binding, for example by adsorption. International patent applications WO 92/07023, WO 92/07006 and WO 92/05201 are examples which develop a technique in which a support is coated with an uncharged hydrophilic polymer: epoxy PEG (polyethylene glycol), covalently bonded to a polyethylene imine (PEI). The process described in those three patent applications is carried out in a non polar reaction medium; the epoxy PEG forms a stable bond with the PEI which, by direct reaction by reducing the pH of the reaction medium, becomes bound to the insoluble support. An epoxy type functionalised support is thus obtained; however, such supports have the disadvantage of sometimes being too hydrophilic due to the presence of the hydroxyl groups and such an excess hydrophilic nature can prevent a protein which is to be used as a ligand from coming into contact with the reactional epoxy groups with the result that the degree of binding of the ligand on the support is reduced.

To eliminate this problem, a microemulsion containing the ligand has been developed to encourage contact between the ligand and a hydrophilic support (WO 92/07023).

One particular application for binding biological macromolecules on supports which has long been envisaged is the specific purification of fluids with the aim of eliminating molecules or macromolecules. A particular example is immuno-purification of plasma proteins. This is normally carried out by passing plasma, and less frequently blood, obtained from donors over a solid support to which a ligand is bonded which can specifically react, and if possible with high affinity, with the molecule which it is desired to obtain.

Particularly suitable ligands for purification are monoclonal antibodies. They have proved their worth for specific in vitro immuno-purification in numerous applications in affinity chromatography (Current Protocol in Immunology, Section II, Unit 8-2) by the specificity of their interactions with antigens and their high affinities with the corresponding antigens. However, extracorporeal immuno-purification with the aim of maximum elimination of the substance from the plasma fundamentally differs from in vitro purification with the aim of obtaining a purified and/or concentrated substance on a number of points, in particular:
the required biocompatibility of the modified support as mentioned above;
covalent binding of the ligand by a method which enables its functional integrity to be preserved;
the affinity of antibodies for their epitopes must be such that precipitation of the antigens into the circulation is minimal, while in vitro immuno-purification to obtain purified substances must allow precipitation without denaturing those substances, at the risk of a lower binding yield.

The only commercially available product which can be cited as an example of extracorporeal purification is a column composed of protein A grafted onto sepharose beads and sold as an Immunosorba column (Excorim). Protein A, extracted from the wall of *S. aureus,* has an affinity for the Fc fragment of IgG, so Immunosorba columns have a very limited application in that only IgG, but all IgG compounds without distinction for their antigenic specificity are eliminated, which is clearly not the desired aim in the majority of cases.

The inventors wanted to use the advantageous physical and functional properties of existing systems for extracorporeal circulation to purify biological fluids, in particular plasma; such purification could represent a therapy to eliminate molecules or macromolecules the presence of which leads to certain pathologies or certain biological dysfunctions, more particularly, toxic molecules and macromolecules with a molecular weight which is higher than that of albumin (66 400 daltons) and which are not eliminated by hemofiltration or hemodialysis techniques.

The present invention provides a module for extracorporeal purification of a biological fluid, comprising a compartment for circulating said fluid; said compartment is at least partially delimited by a functionalised support or a wall the surface of which comprises functionalised groups, and which satisfies the following conditions:
it is stable at at least a temperature in the range about 15° C. to about 45° C.;
it is hemocompatible;
it is stable to at least one type of sterilisation process which can be applied to medical apparatus; in particular gamma radiation;
if necessary, in the presence of an activating substance it can develop functional groups which can form covalent bonds with ligands carrying the
groups:

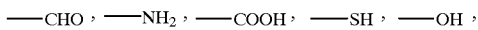

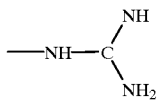

it must have a sufficient hydrophilic nature to prevent non specific binding of macromolecules, but less than a critical threshold above which the covalent degree of binding of the ligands will be low if not zero. The hydrophilic nature can be intrinsic or conferred by chemical modification.

The term functionalised support as used here will be used for any wall or surface comprising groups which are stable at room temperature and for a period compatible with commercial use and capable, in the presence of an activating substance, of generating functional groups which are themselves capable of reacting with organic groups of the type —CHO, —NH$_2$, —COOH, —SH, for direct or indirect coupling of a ligand, which is itself capable of specifically interacting with particular molecules or elements of a biologic fluid which is to be purified.

Any dialysis membrane can in particular constitute the basis of functionalized supports in the form of a flat film or hollow fibres; in the form of a flat film or solid or hollow non porous fibres; in the form of porous or non porous microbeads, or a combination of the above.

The module for extracorporeal purification of a biological fluid can also comprise a functionalized support the surface of which carries charges, by means of which molecules or macromolecules of a first type are bonded by ionic bonds, which molecules or macromolecules, once bonded, exhibit free amine groups to which are covalently bonded molecules of a second type which, once bonded, exhibit free carboxylic groups 1) which can form amide, ester and thioester bonds with $NH_2$, OH and SH groups respectively; or 2) which can be modified to hydrazines to form hydrazone bonds with aldehydes; or 3) which can be modified to amines to form imines with aldehydes and which can be stabilised to amines by reduction; or 4) which can be modified to a 1,2-diketone (for example cyclohexanedione, glyoxal, etc . . . ) to be above to form covalent bonds with

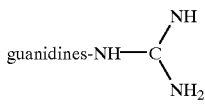

One example of molecules of the first type is a polyethyleneimine with a molecular weight in the range 10 000 to 2 000 000 daltons.

One example of molecules of the second type is a dicarboxylic acid anhydride with formula:

where $X=[CH_2]_n$, n being equal to 2 or 3, or $X=-CH=CH-$.

A further example of a molecule of the second type is a monocarboxylic acid anhydride such as that of acetic acid, with formula:

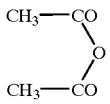

For application to specific biological purification, the free carboxylic groups can form amide bonds either with the ligand enabling specific biological purification, or with a third type of molecule which can have one or more of the following functions:

add a spacer to reduce steric hindrance and encourage subsequent binding of a ligand and/or the molecule or set elements to be purified;

increase the hydrophilic nature of the membrane or support to limit non specific interactions with proteins or with any substance which is susceptible to such interactions;

exhibit a group of another nature, for example an amine group, enabling another type of covalent coupling with a ligand carrying the following groups: —CHO, —COOH, $-NH_2$.

These different functions can be combined in a single molecule. One advantageous example of a third type molecule which combines the three above functions is a dihydrazide with formula:

$NH_2-NH-CO-Y-CO-NH-NH_2$ where Y is preferably a $(CH_2)_m$ group where m is in the range 2 to 6.

Further, Y must be selected so that it carries hydrophilic groups, but in no case can it be a complement activator, and it must be stable to at least one method of sterilizing medical apparatus, such as gamma radiation.

The use of a module of the invention in an extracorporeal circuit implies that the supports have certain intrinsic properties of the supports, namely:

minimum non specific adsorption;

an absence of activation of the contact phase, i.e., a kallikrein generation of less than 10 units per liter;

non-toxicity.

Further, to use it for specific biological purification, they must have a high coupling capacity with specific ligands.

The modules produced from said supports must enable a biological fluid to circulate under conditions which are compatible with the envisaged therapeutic approach.

The modules of the invention will preferably comprises as a membrane, a semi-permeable membrane produced from a copolymer of acrylonitrile and sodium methallyl sulphonate, type AN69.

The present invention also provides a process for preparing a functionalized biocompatible support carrying groups which can form covalent bonds with organic groups, in particular:

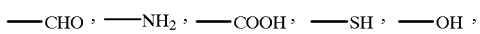

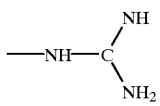

and comprising the following steps:

a) bringing supports comprising bound anionic groups into contact with a polyethylene imine (PEI) with a molecular weight in the range 10 000 to 2 000 000 daltons, the PEI being substituted or non substituted;

b) bringing the treated support of a) into contact with a solution of a dicarboxylic acid anhydride with formula:

where $X=[CH_2]_n$, n being equal to 2 or 3, or $X=-CH=CH-$, or a monocarboxylic acid anhydride such as that of acetic acid with formula:

The terminal carboxy group can be directly used for coupling with a ligand, either by adding a carbodiimide, or by converting the carboxy group to an activated ester in the form of N hydroxysuccinimide.

c) if required, bringing the support modified by steps a) and b) into contact with a dihydrazide with formula:

$NH_2-NH-CO-Y-CO-NH-NH_2$ in the presence of an coupling agent which activates carboxy groups, such as carbodiimides.

Y is selected from groups which do not activate the complement and are stable to at least one method for sterilising medical apparatus such as gamma radiation. Y is preferably a $[CH_2]_m$ group where m is in the range 1 to 4.

This first variation of the process of the invention will hereinafter be termed post-acylation.

The process of the invention includes a variation leading to an equivalent result in which the carboxylic anhydride of step b) has reacted with the PEI of step a) before treating the support as proposed in step a); in other words, in this variation a functionalized biocompatible support carrying groups which can form covalent bonds with organic groups, in particular:

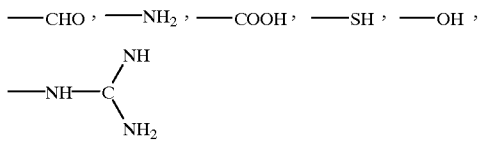

can be obtained by bringing supports with an ionic nature into contact with the product of the reaction between: a polyethylene imine (PEI) with a molecular weight in the range 10 000 to 2 000 000 daltons, said PEI being substituted or non substituted, with a solution of a dicarboxylic acid anhydride with formula:

where X has the same meaning as that given above, or a monocarboxylic acid anhydride with formula:

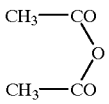

The modified support is then brought into contact with a dihydrazide with formula:

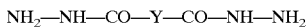

$NH_2—NH—CO—Y—CO—NH—NH_2$ where Y has the same meaning as that given above.

In either of the above processes, the anionic support is preferably a membrane constituted by a copolymer of acrylonitrile and sodium methallyl sulphonate type AN69 as described above. The PEI preferably has a molecular weight in the range 10 000 to 2 000 000 daltons.

The dicarboxylic acid anhydride is preferably that of succinic acid with formula:

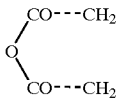

The anhydride is used in solution in a concentration of 0.5 M to 2 M in acetonitrile. This second variation is termed pre-acylation to differentiate it from the first variation.

After coupling either the acetic anhydride or the succinic anhydride with the PEI via an amide bond, the ensemble is brought into contact with the anionic support. When treating with pre-succinylated PEI, the —COOH functions can react with the dihydrazide which is preferably ADH (adipic dihydrazide) where m equals 4.

More generally, the invention relates to supports which can be obtained by the process or its variation described above, and to biological purification modules comprising the support. These supports must satisfy the same conditions as those listed above.

The processes of the invention described above can be carried out to prepare dialysis and/or hemofiltration membranes. The invention concerns membranes which can be obtained by these processes, whether they consist of post-acylation of PEI or pre-acylation thereof.

Dialysis modules comprising the membranes thus formed form part of the invention.

The ligands which can be coupled to the functionalized supports can be homogeneous or heterogeneous in nature, i.e., they can be constituted by a single molecular species or a compatible mixture of a plurality of molecular species if the biological fluid is to be purified of a plurality of molecules simultaneously, or a single molecule with ligands which have a different affinity for different sites thereof; for example, when the ligand is an antibody or an antibody fragment, it may be a mixture of antibodies of different specificities. Bringing a biological fluid into contact with the support modified by covalent bonding of the ligands enables one or more molecular or macromolecular species, or a particular element of the biological fluid with an affinity for the ligand(s) to be selectively eliminated.

The ligands will be covalently bound using any known means, by the action of an activating substance compatible with extracorporeal use of the modified support. Such means have been described in the following documents: United States patent U.S. Pat. No. 4 217 338; Thomas et al., Colloids and Surfaces A (1993), vol. 77; 125–139; Malmsten et al., J. Colloid and Interface Science (1996), vol. 177; 70–78.

The figures in brackets correspond to the bibliographical references listed at the end of the description.

When the ligands are antibodies, two approaches are possible: the first consists of coupling the antibodies via an amide bond between the amine groups of the antibodies and the carboxy groups of the supports.

The second consists of oxidizing the antibodies using sodium periodate, then coupling them by forming a hydrazone bond between the aldehyde groups produced on the carbohydrate groups of the molecule and the hydrazide acids of the support functionalised by dihydrazides; the coupling efficiency under these conditions is a maximum when the pH is in the range 4 to 6.

One example of each of these approaches is shown in FIGS. 1 and 2.

It would be pointless to list all of the situations in which biological purification of biological fluids would be of therapeutic interest because the steady development of knowledge regarding metabolic and pathological processes is constantly providing new candidates for purification; the skilled person will be able to select the appropriate ligand or mixture of ligands depending on the therapeutic decision made; as an example, he could if necessary combine mixtures of antibodies of different epitopic or antigenic specificities when eliminating complex molecules or mixtures; finally, he could choose to purify the biological fluid using a ligand with an affinity not for the substance to be eliminated but for a further substance specifically complexed with that which it is desired to eliminate.

The antibodies can be polyclonal antibodies or, as is preferable, monoclonal antibodies, either monospecific or a mixture of several epitopic or molecular specificities. Examples are:

anti-cytokine pro-inflammatory antibodies (IL-1β; TNFα; IL-6) for treatment of septic shock or for the treatment of inflammatory phenomena such as rheumatoid polyarthritis;

anti RhD antibodies for the treatment or prevention of hemolytic disease of newborn;

anti-HLA antibodies, in organ graft prophylaxia.

Specific elimination of particular elements of the blood such as cells or platelets using suitable ligands such as antibodies, receptors, lectins, etc., may also be desired.

The products of coupling between the functionalised supports of the invention and the ligands, in particular monoclonal or polyclonal antibodies, are novel and also form part of the invention, as well as their use for purifying biological fluids.

In order to be effective, the coupling product must be characterized by an optimum quantity of bound antibodies which is variable for each type of antigen. As an example, about 2 mg/m² can be bound.

Antigens also represent an important candidate for purification in biological fluids, in particular in the case of autoimmune diseases, for eliminating autoantibodies.

Autoimmune pathologies currently represent the third largest pathological process after cardiovascular disease and cancer, and for which only symptomatic treatments exist.

Above all, autoimmune diseases are marked by B lymphocyte hyperactivity and in addition to other biological symptoms are characterized by the presence of multiple autoantibodies directed against autoantigens. Examples are various nuclear anti-antigen antibodies, anti DNA antibodies, antibodies against enzymes and nucleoproteins involved in RNA transcription and translation processes. Typical examples of autoimmune diseases are systemic lupus erythematosus (SLE) or rheumatoid polyarthritis. The wide diversity of autoantibodies which can be present in several systemic pathologys renders diagnosis very difficult, more so as clinically, the symptoms are sometimes mixed.

While autoantibody production appears to be a characteristic in patients with autoimmune diseases, it is interesting to note that this production also increases with age in healthy individuals (8, 14, 18) without these individuals developing autoimmune diseases. Further, target autoantigens (DNA, histones, enzymes and nucleoproteins) of autoantibodies produced in the same individuals are the same as those seen in autoimmune diseases, in particular in SLE (11).

In contrast, a number of studies have established the pathogenic character of immunocomplexes. It has been shown that kidney failure, one of the ultimate causes of death in patients with SLE, is induced by deposits of immune complexes in the kidneys and in particular DNA/anti-DNA immune complexes (9, 10). Recently, Sasaki et al. used certain elements to associate the presence of DNA/antiDNA immune complexes with the incidence of diffuse proliferative glomerulonephritis, hence the interest in eliminating the antigens and antibodies involved in the formation of circulating immune complexes before any renal complications can occur in order to reduce their formation in patients.

The principal different therapeutic routes currently used are:
a) treatment with glucocorticoids which in high doses (0.7 to 1 ml/kg) cause a clear clinical improvement with a reduction in the number of the various autoantibodies, the disappearance of immune complexes and a rise in the level of seric complement;
b) immunosuppressors, the use of which is more controversial;
c) plasma exchange or plasmaphereses.
   while the last technique has proved to be effective for some patients with lupus, it has a number of disadvantages: it is expensive, difficult to carry out, elimination is non selective as it removes not only pathogenic immune complexes but also essential constituents such as immunoglobulins, coagulation factors, complement molecules, and many other compounds with a regulating activity. It is thus far more traumatic for the organism than a specific technique.
   Finally, the treatment is often followed by rebound phenomena where the number of immune complexes and autoantibodies dramatically increases a few days after treatment is stopped;
d) apheresis which is normally carried out by passing plasma, or more rarely blood, over a solid support on which a ligand is bonded which can specifically react, if possible with high affinity, with sites present on target cells or on low or high molecular weight constituents.

In the case of SLE, one possible therapy consists of specifically eliminating pathogenic antibodies, in this case anti-DNA antibodies, using this process. The first data were supplied by Terman et al. who used a column of colloidal DNA to purify the blood of patients with lupus. However, the use of DNA as a ligand remains very limited partly because of its instability in contact with enzymes such as nucleases and plasmatic esterases and partly because of the potential danger linked with its potentially transforming nature which could result in its precipitation in the circulation, complexed with seric proteins. However, anti-DNA antibodies can be specifically trapped not by DNA but by other compounds with which these antibodies cross-react. A number of authors, among them Lafer et al., and Shoenfeld, have shown that murine and human anti-DNA antibodies are capable of reacting with compounds which are very different to DNA such as cardiolipin or other negatively charged phospholipid molecules; Suzuki et al. designed a continuous apheresis system using a dextrane sulphate gel coupled with a support regeneration system and demonstrated a reduction in the number of anti-DNA antibodies in patients with lupus. However, the importance of that therapeutic strategy appears to be limited by the fact that only anti-DNA antibodies are partially eliminated and they are not the only autoantibodies at the origin of the lesions encountered in lupus.

Lipoic acid (LA) or 6,8-thioctic acid (TA) is a molecule containing eight carbon atoms bonded to two atoms of sulphur on carbons 6 and 8 to form a dithiolane heterocycle.

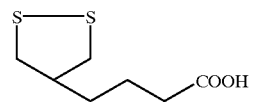

Metabolically, it constitutes an essential cofactor for dehydrogenase oxo acids which are multi-enzymatic complexes essential for enzymes such as pyruvate dehydrogenase (PDH) or oxoglutarate dehydrogenase; it covalently bonds to the $NH_2$ groups of the lysine (1, 2, 21).

Immunologically, it has clearly been shown that the portion of PDH corresponding to the binding site of lipoic acid constitutes an autoantigen which can be recognised by autoantibodies in patients with primary biliary cirrhosis (7). Recently, some authors have shown that the presence of lipoic acid on this autoantigen is determining for this recognition in patients (6, 7).

Still in the immunological field, it has been shown that compounds carrying sulphhydryl groups, among them 2-mercaptoethanol and dithiothreitol, are capable of stimulating the production of antibodies in cultured lymphocytes (3, 4, 15, 17).

Ohmori has studied the effect of LA in vitro with the aim of defining its possible immunostimulating character (16). It appears clear that the increase in the antibody response following antigenic stimulation in the presence of LA is dependent on the T population. A reduction in auxiliary T lymphocytes cancels the action of LA. Further, the stimulation obtained is specific to the antigen used.

The choice of lipoic acid as a ligand in treating SLE by immuno-purification is based on the following observations:
1) Serum from patients with SLE contain large quantities of anti-LA antibodies of the IgG class but particularly of the IgM class, which is different from normal subjects as shown in FIG. 3;
2) The quantity of anti-LA antibodies increases in the serum of MRL/lpr mice with age; further, these mice spontaneously develop SLE on aging. A comparative study of the quantity of anti-LA antibodies in the MRL/lpr mouse and control mice, termed MRL/mp mice, as a function of the age of the animals clearly showed that the number of anti-LA antibodies increases from the twelfth week in the MRL/lpr mouse while this number remained low in the MRL/mp control mouse. The results are shown in FIG. 4.
3) Anti-LA antibodies react with double strand DNA but not with single strand DNA (13); SLE is characterized by the presence at a given moment of the disease of double strand anti-DNA antibody.
4) Purification of anti-LA antibodies from the serum of a patient suffering from SLE simultaneously reduces the number of double strand anti-DNA antibody (FIG. 5).

From the observations and the results described above, lipoic acid would appear to be an excellent candidate for purifying the plasma of anti-LA antibody and anti-DNA antibody in lupus pathology.

Lipoic acid can be coupled to the functionalized support via amide bonding with amine groups produced by a monohydrazide, a dihydrazide, or a diamine with formula $NH_2$—$(CH_2)_n$—$NH_2$ where n is in the range 2 to 6, or by a polyamine with formula $NH_2$—$(CH_2)_x$—$NH$—$(CH_2)_y$—$NH_2$ where x and y are in the range 3 to 6, for example. Examples of the coupling of the invention with lipoic acid for the treatment of SLE are given in the examples below.

The invention also relates to the coupling product between a functionalized support of the invention and lipoic acid, and its use in purifying the serum of patients with SLE. Apparatus comprising this coupling product perform particularly well in treating autoimmune diseases, more particularly SLE.

Depending on the case, the skilled person will be able to select the appropriate ligand for therapeutic treatment of a given pathology by selecting the ligand from a group constituted, in addition to the antibodies and antigens described above, by peptides, glycoproteins, hormones, enzymes, cofactors thereof, substrates or inhibitors thereof, polysaccharides, lectins, toxins or antitoxins, nucleic acids or polynucleotidic acids, haptens, haptene ligands, pigments or stains.

Treatment of a given pathology can be carried out by mixing ligands either simultaneously or sequentially by using a plurality of coupling products.

The present invention encompasses the use of a functionalized support as described above and resulting from carrying out the processes of the invention to produce a multipurpose module for extracorporeal purification of biological fluids, from which biochemical species or cells present in biological fluids are removed, and the removal of which is desired, in particular antigens, antibodies or haptenes.

The present invention also relates to a multipurpose kit for preparing a coupling product of the invention between the functionalized support and one or more specific ligands for the purification of biological fluids, said kit comprising at least:

1) a device comprising a support which can be covalently coupled to a ligand;
2) a sterile pouch or receptacle containing an solution for activating the reaction between the functionalized support and the ligand;
the ligand, in a suitable solution and at a suitable concentration;
if required, one or more rinsing solutions.

One embodiment of the kit of the invention is shown in FIG. 10 and consists of a therapeutic solution combining a modified support which can be obtained by a process as described above, the porosity and modification of the support being adapted to the ligand and to the nature and concentration of the molecule(s), or of set elements which are to be eliminated from the biological fluid.

In the kit, the device can advantageously be a dialysis cartridge, more particularly a functionalized AN69 cartridge as described above.

When the ligand in the kit of the invention is lipoic acid, and the groups present on the support are amine groups, the activating solution will preferably be a carbodiimide in hydrosoluble form.

When the ligand in the kit of the invention is an antibody, the activating solution is sodium periodate, for example. The reactions employed in coupling are conventional reactions which are well known to the skilled person who could use higher performance operating conditions, both as regards the nature of the activator and the physicochemical conditions of the reaction, depending on the selected ligand.

The kit of the invention can advantageously be used by care personnel or by qualified personnel associated with them to prepare, in sterile and extemporaneous manner, a cartridge comprising a specific ligand which can be used in an extracorporeal circuit to purify a biological fluid which is preferably blood or plasma.

The invention also encompasses the use of a kit such as that described above in any prophylactic or therapeutic treatment of a mammal, more particularly man.

Finally, the invention encompasses a specific process for biological purification of human or animal blood or plasma by extracorporeal circulation in an apparatus comprising at least one module of the invention. In the diagram shown in FIG. 11, whole blood is treated by extracorporeal circulation by passage through a module of the invention and re-administration to the patient. In such a treatment, the possibility exists of ultrafiltering a portion of the blood if necessary.

Further characteristics and advantages of the invention will become more clear from the following examples which are made with reference to FIGS. 1 to 22.

Figure 6:
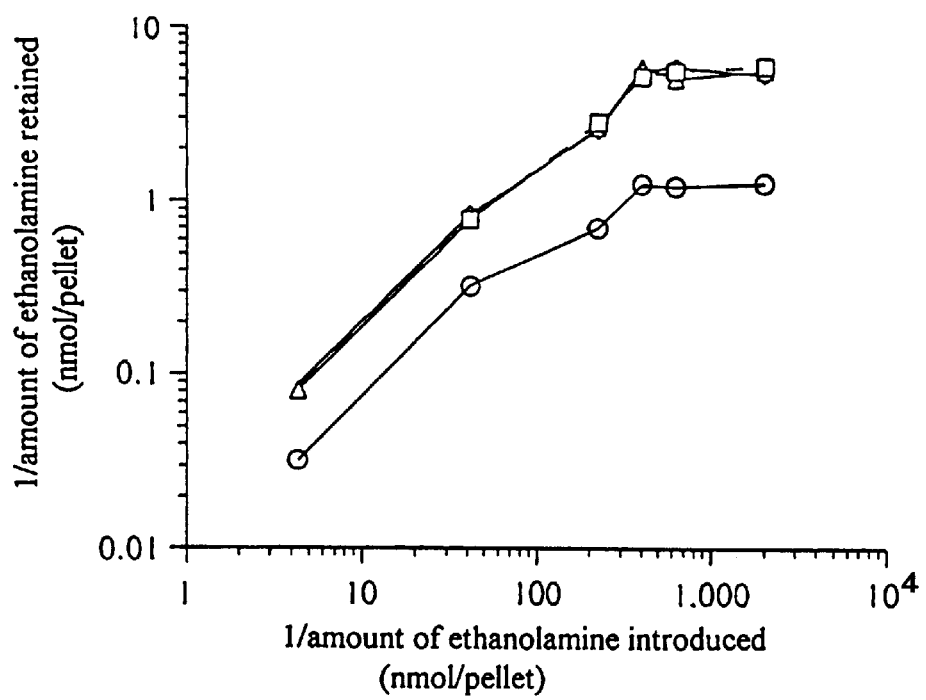

FIG. 6 shows the number of available sites after functionalization of AN69-PEI with succinic anhydride. The curve represents the quantity of anhydrides obtained with respect to the quantity of ethanolamine introduced on succinylated AN69 alone (circle) and succinylated AN69-PEI. Analysis was carried out at the inlet (shown on the curve by a triangle), at the centre (shown on the curve by a lozenge) and at the outlet from the module (shown on the curve by a square).

Figure 7:
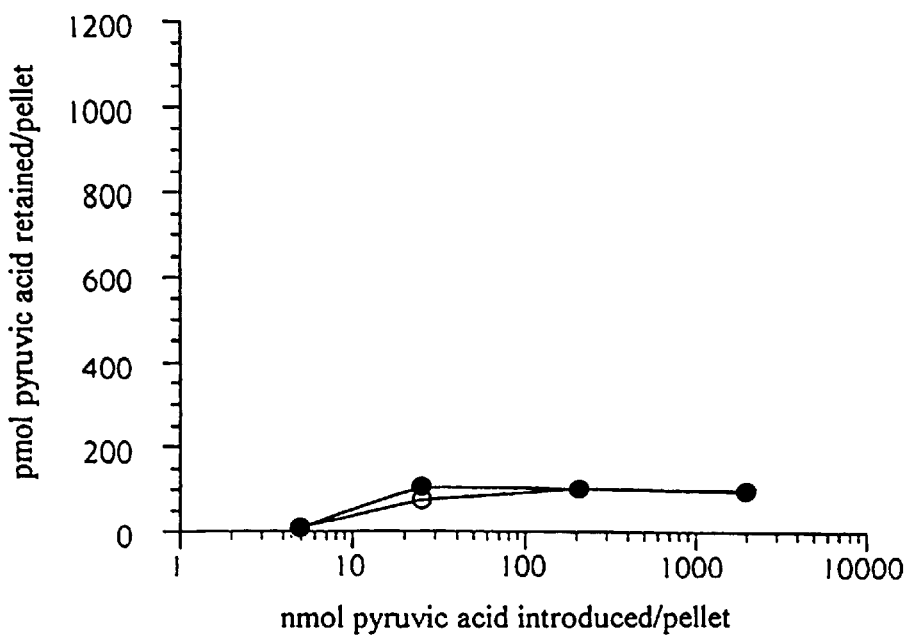
Figure 8:
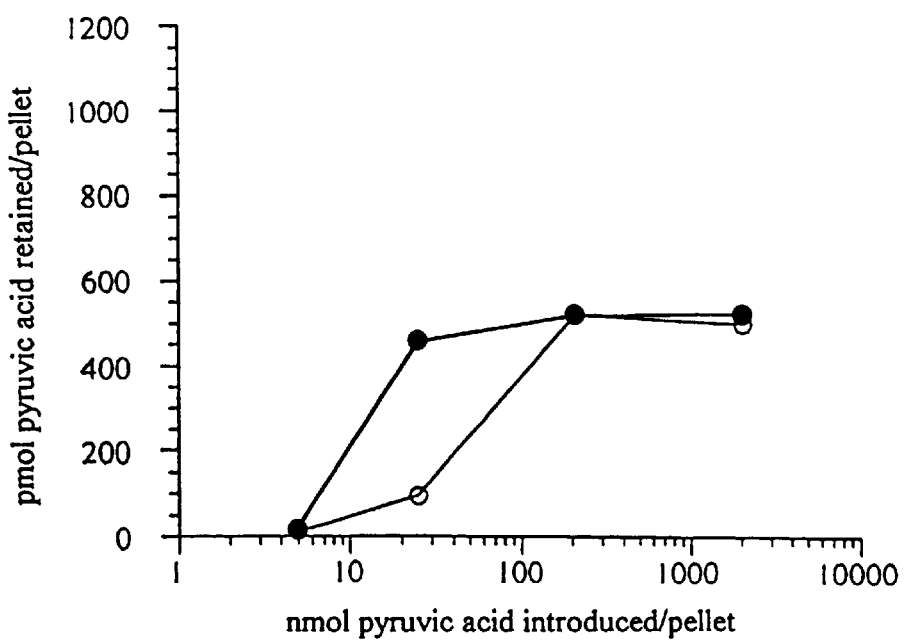
Figure 9:
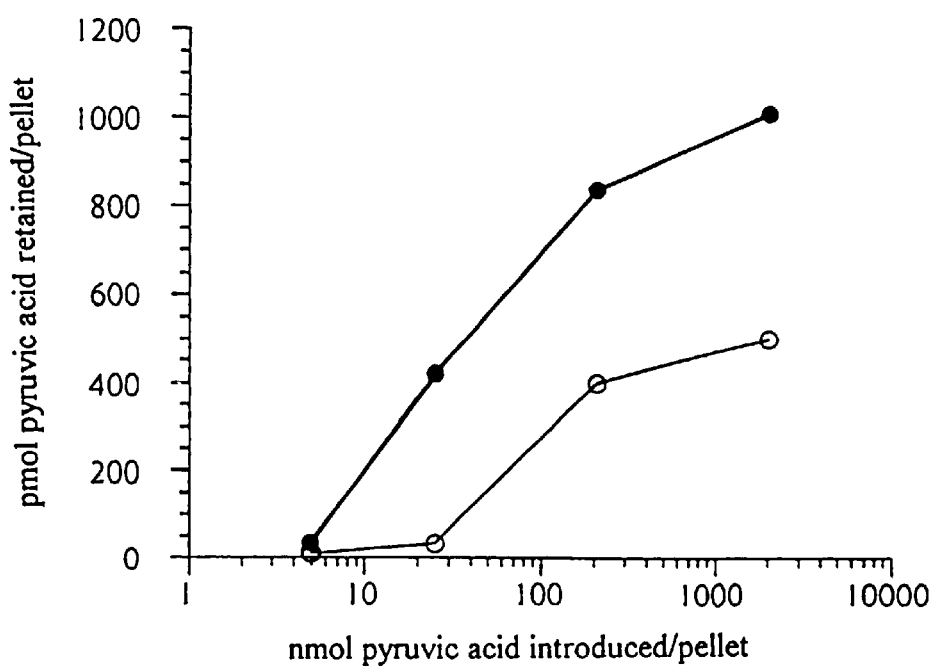

FIGS. 7, 8 and 9 show the binding of $^{14}C$ pyruvic acid on non functionalized AN69 or AN69 functionalised respectively with EDC and ADH, succinic anhydride, EDC and ADH, and PEI, succinic anhydride, and EDC and ADH.

Figure 10:
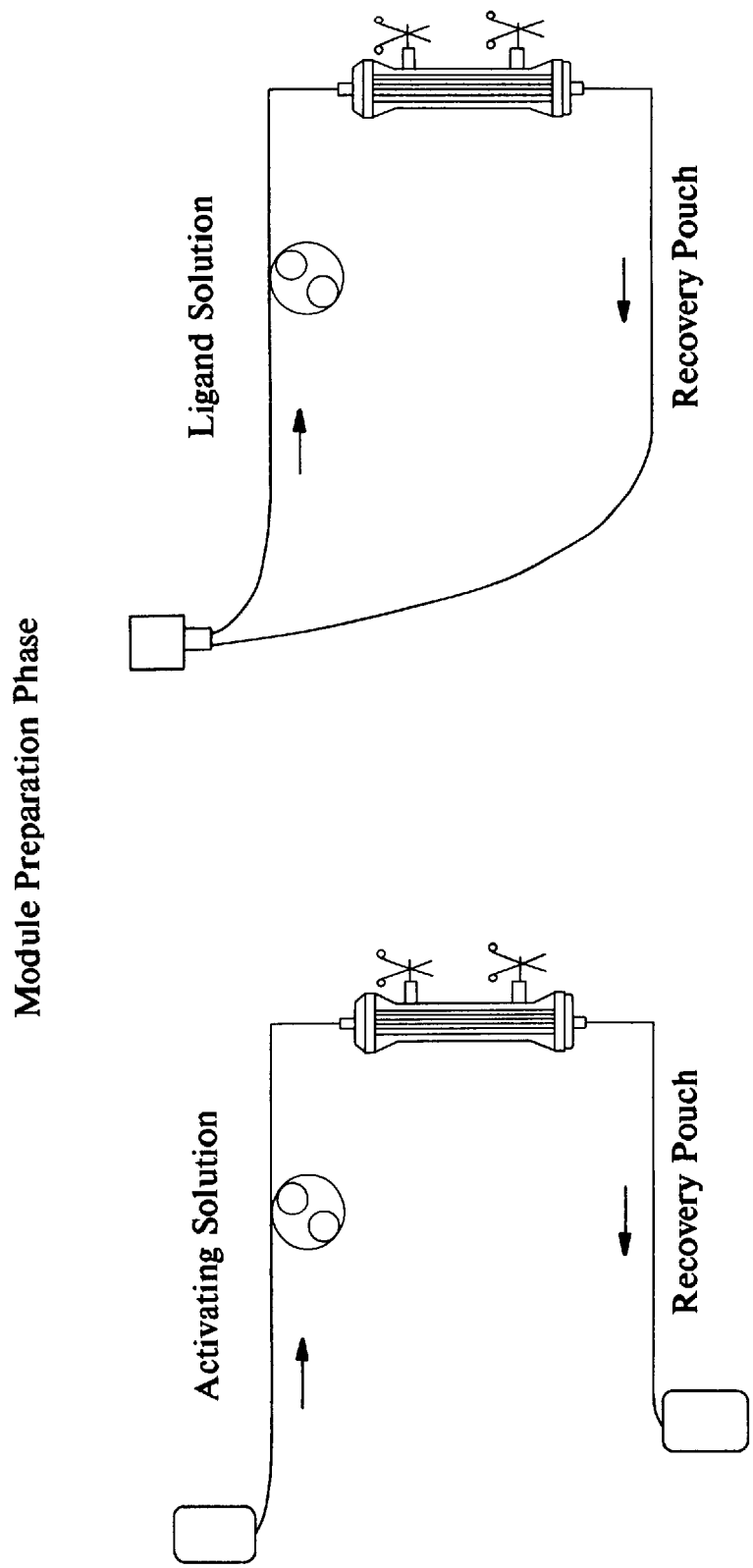
Figure 11:
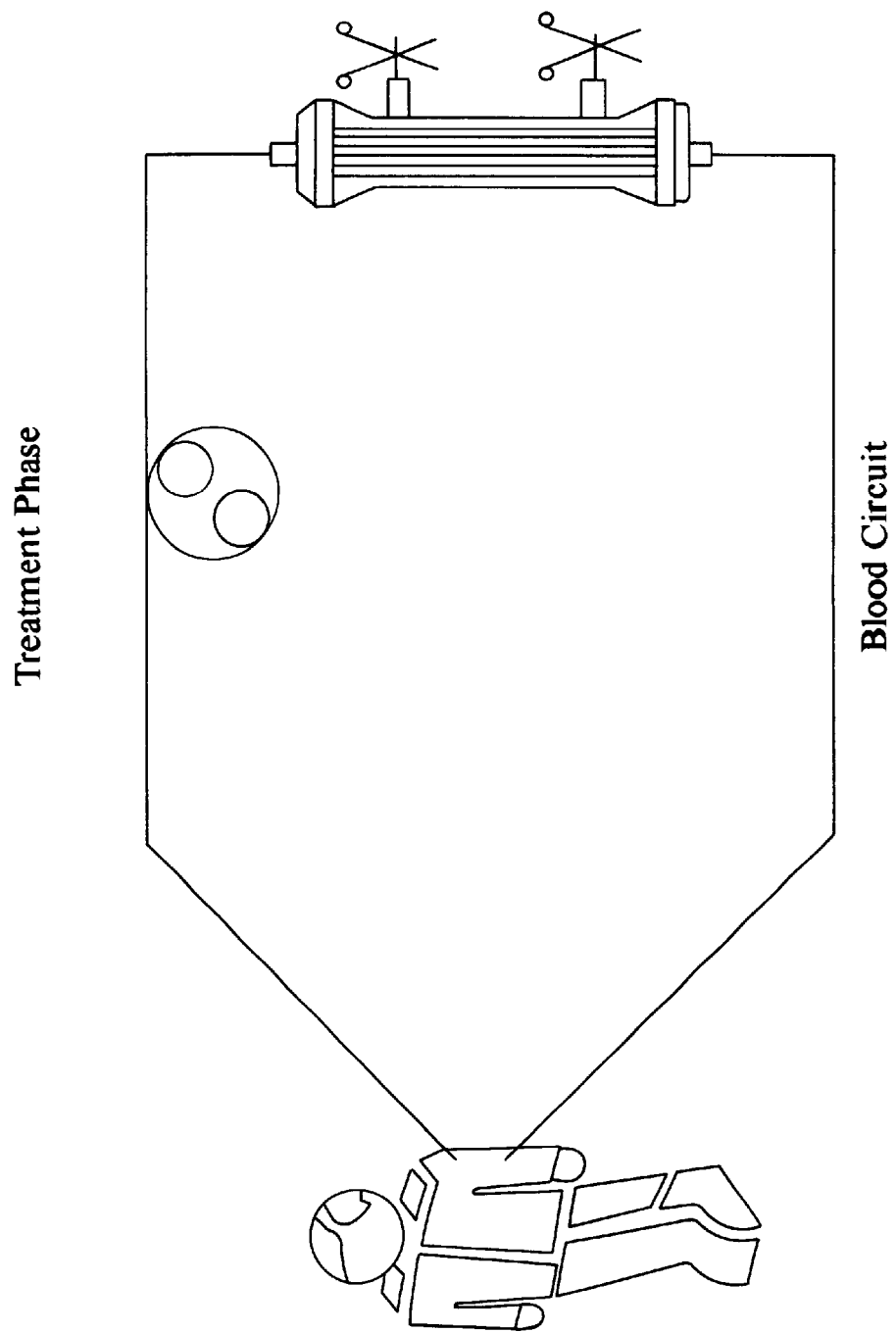

FIG. 10 shows the conditions for preparing a treatment module and FIG. 11 shows the conditions for extracorporeal circulation treatment.

Figure 12:
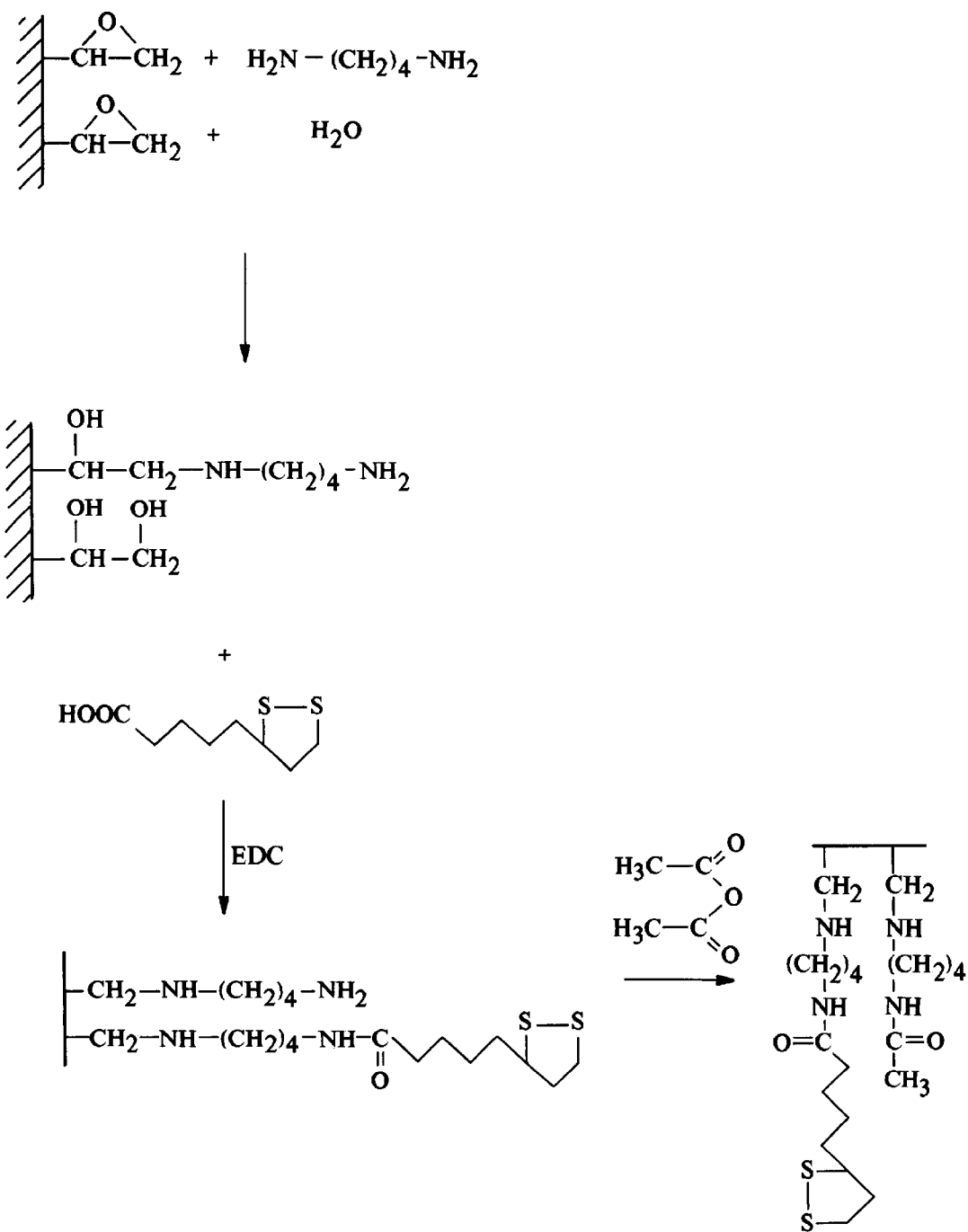

FIG. 12 schematically shows a process for producing a support constituted by an epoxy surface coupled with putrescein, which can form a covalent bond with lipoic acid, in the presence of an EDC activator.

Figure 13:
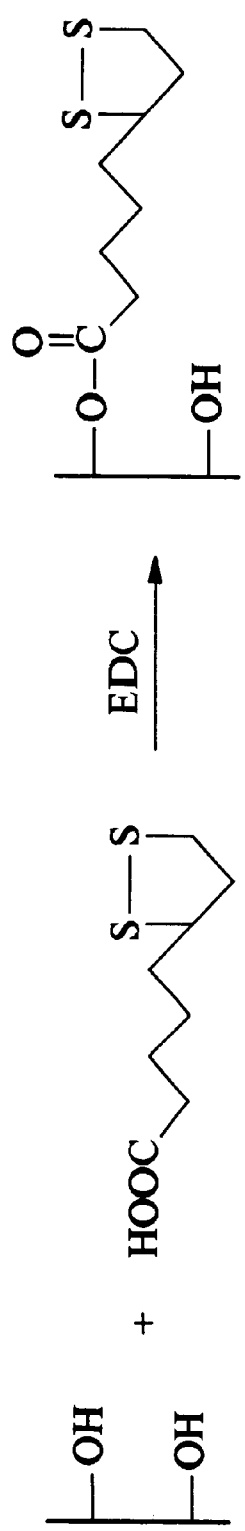

By way of comparison, FIG. 13 shows the formation of the support by an ester bond directly between LA and the OH groups of the epoxy compound.

Figure 14:
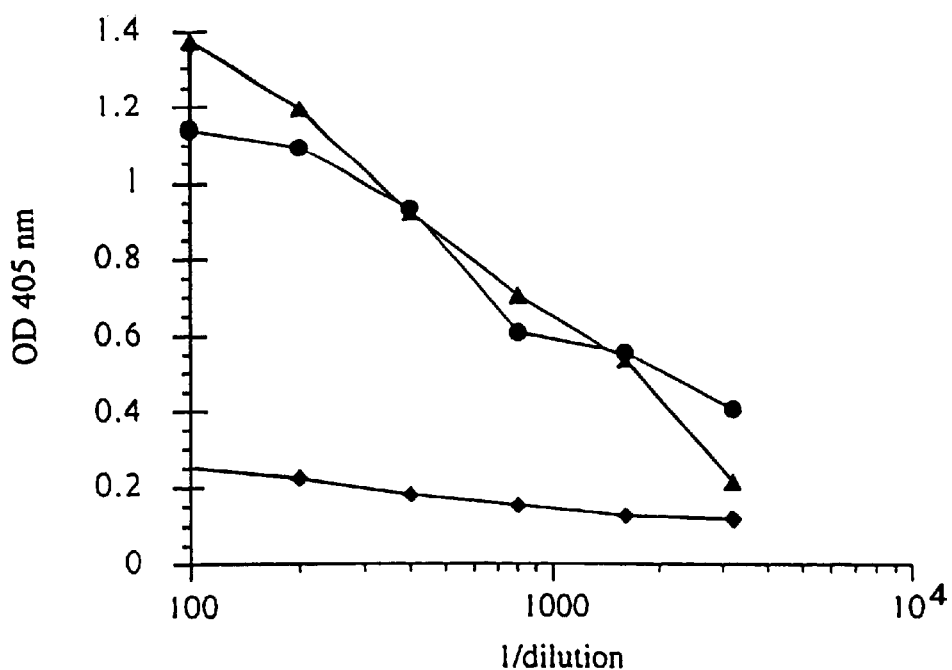

FIG. 14 compares the amount of anti-LA IgM obtained, in other words the purification yields, on an AN69-LA support obtained by ester bonding (black points) or via amide bonding (black lozenges).

Figure 15:
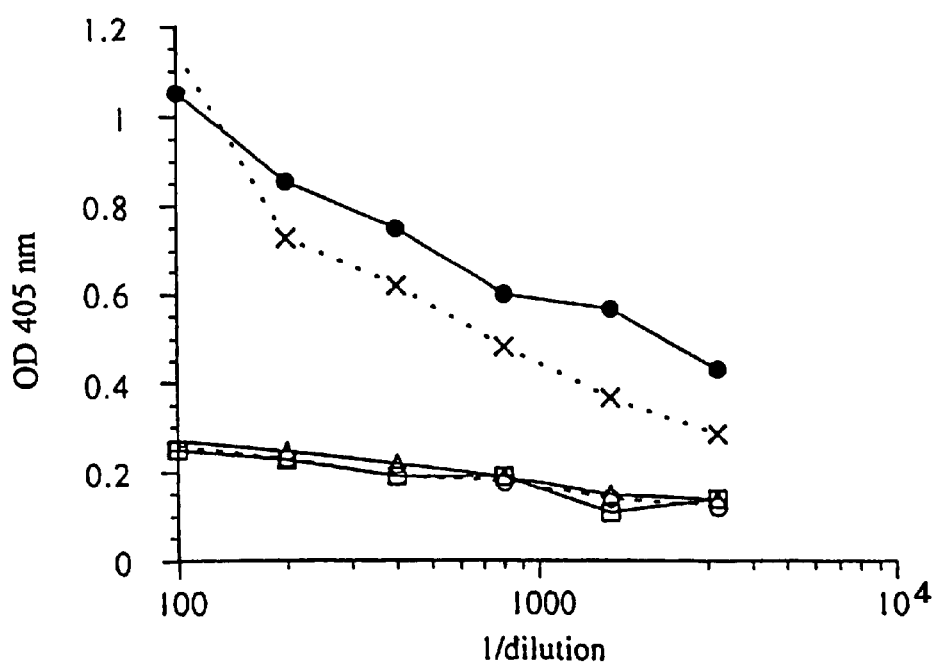

FIG. 15 compares the purification yields obtained after successive passages over columns with a support constituted by AN69-LA.

Figure 16:
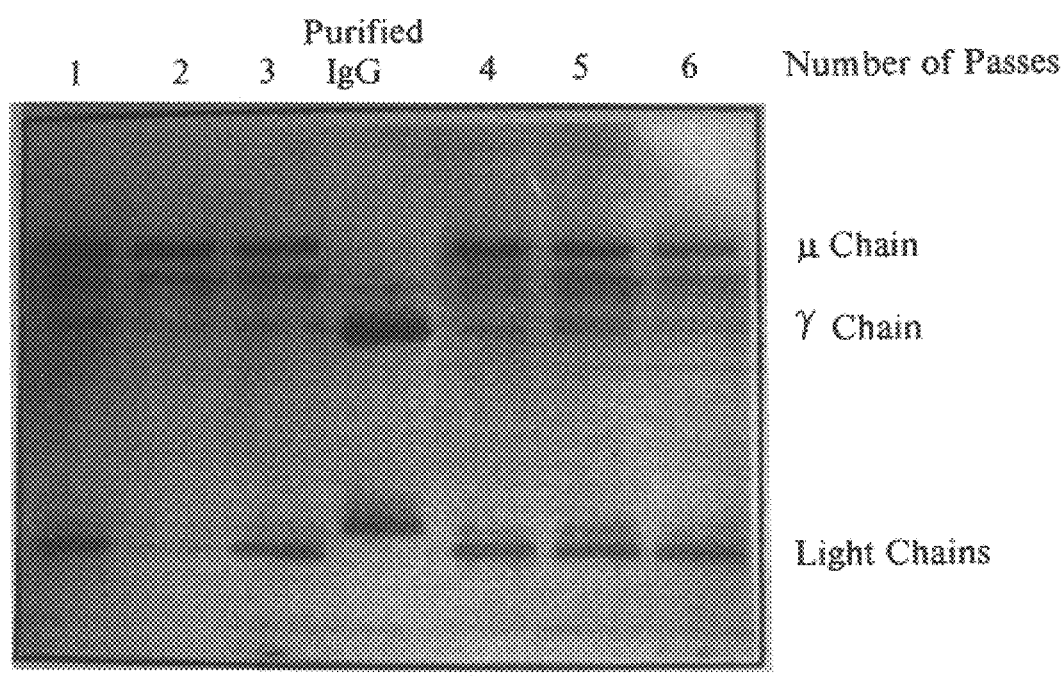

FIG. 16 shows the profile obtained by 10% polyacrylamide gel electrophoresis of proteins eluted after several passages over the same support.

Figure 17:
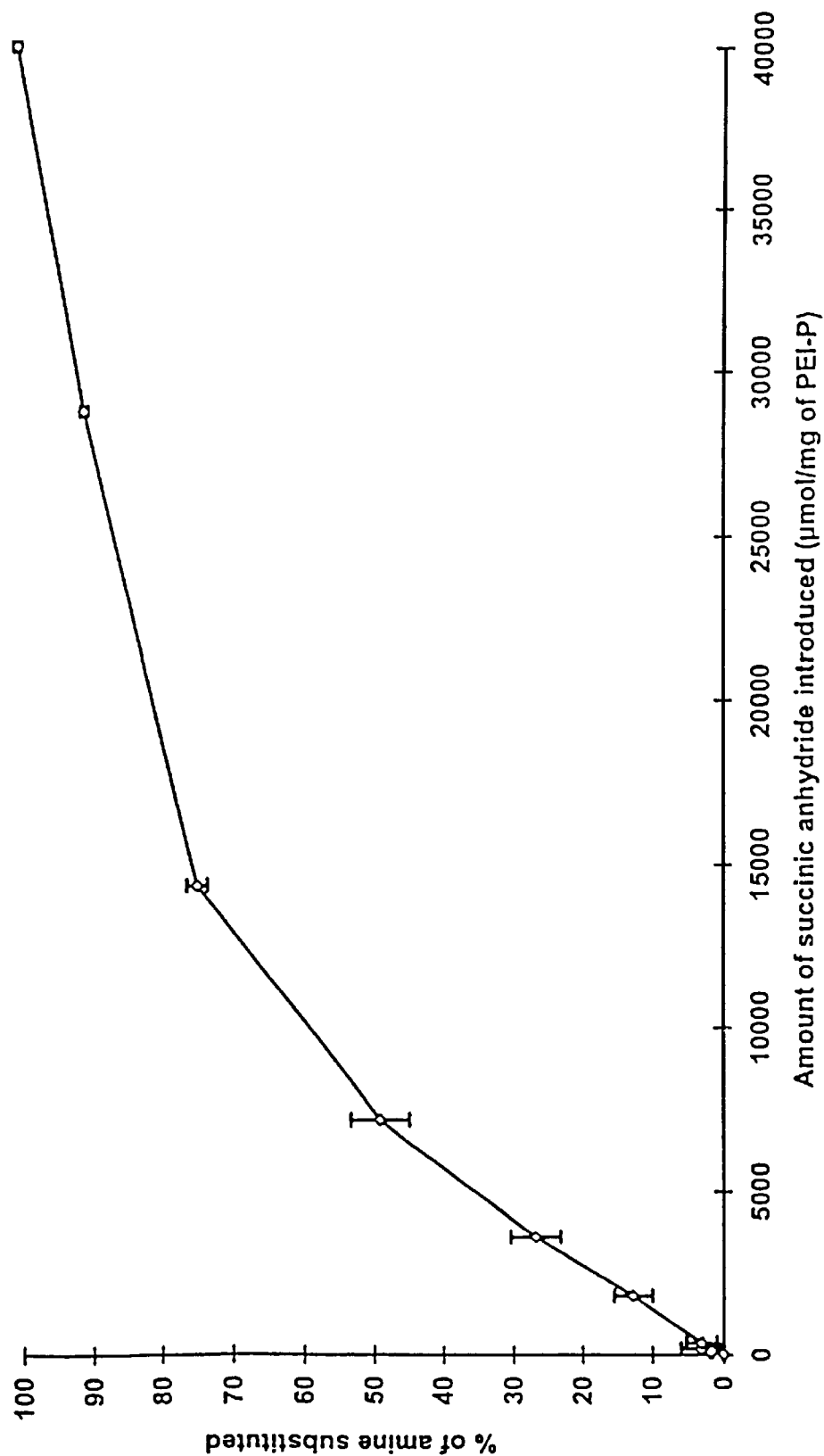

FIG. 17 indicates the amount of substituted amines of the PEI-P as a function of increasing amounts of succinic anhydride reacting with PET.

Figure 18:
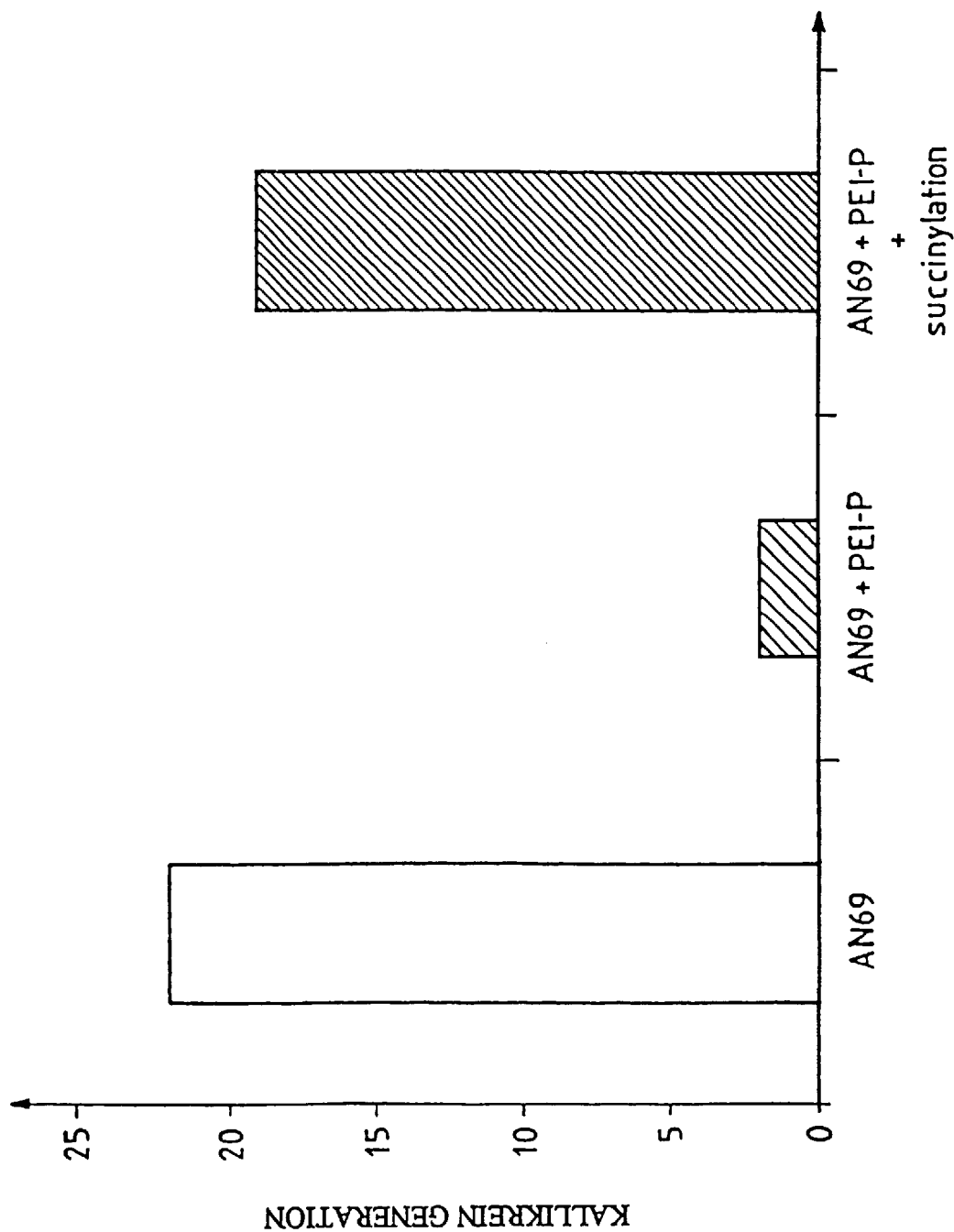

FIG. 18 shows the influence of post-succinylation of PEI-P on contact activation.

Figure 19:
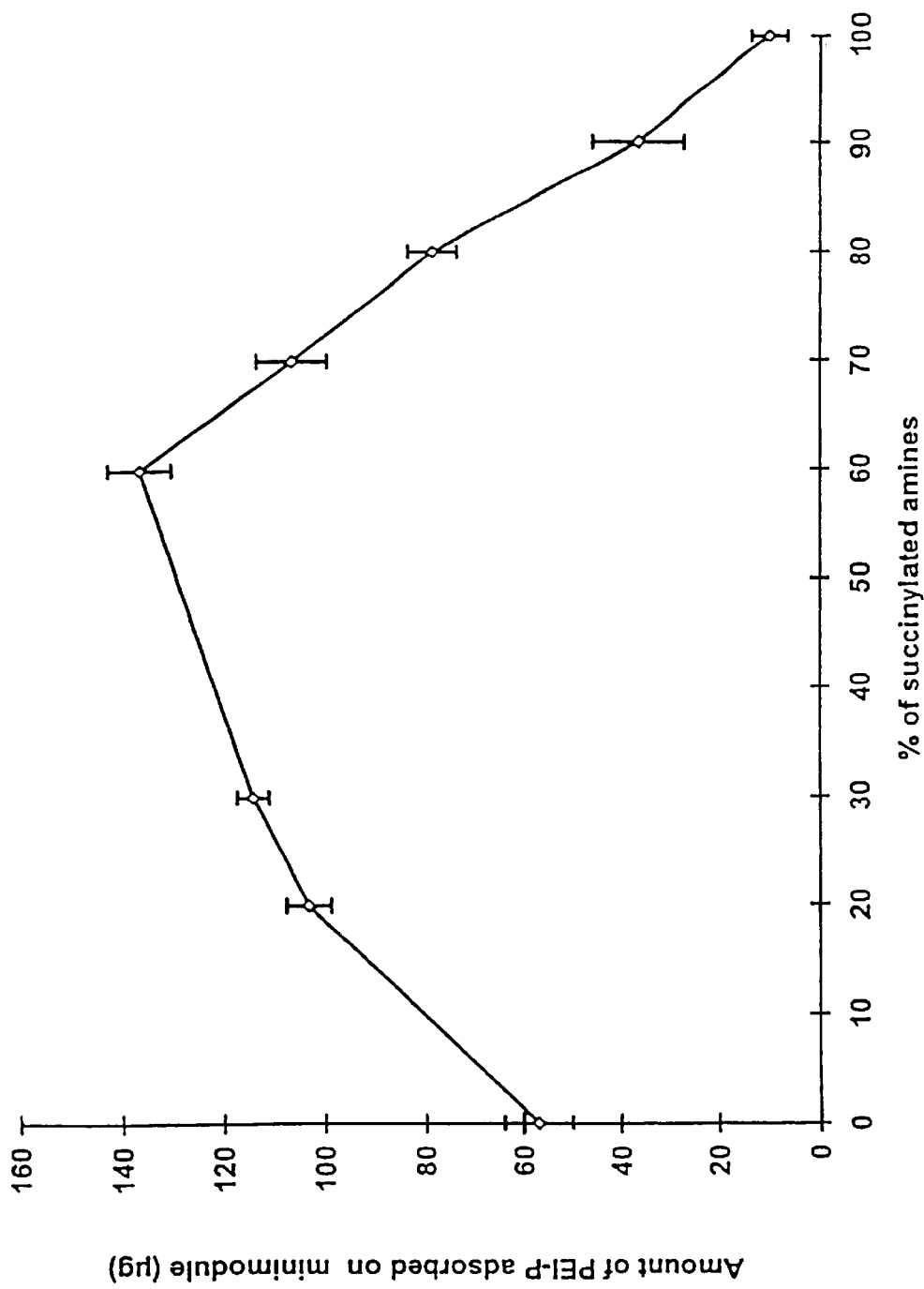

FIG. 19 shows the amount of pre-succinylated PEI-P per AN69 minimodule as a function of the degree of succinylation.

Figure 20:
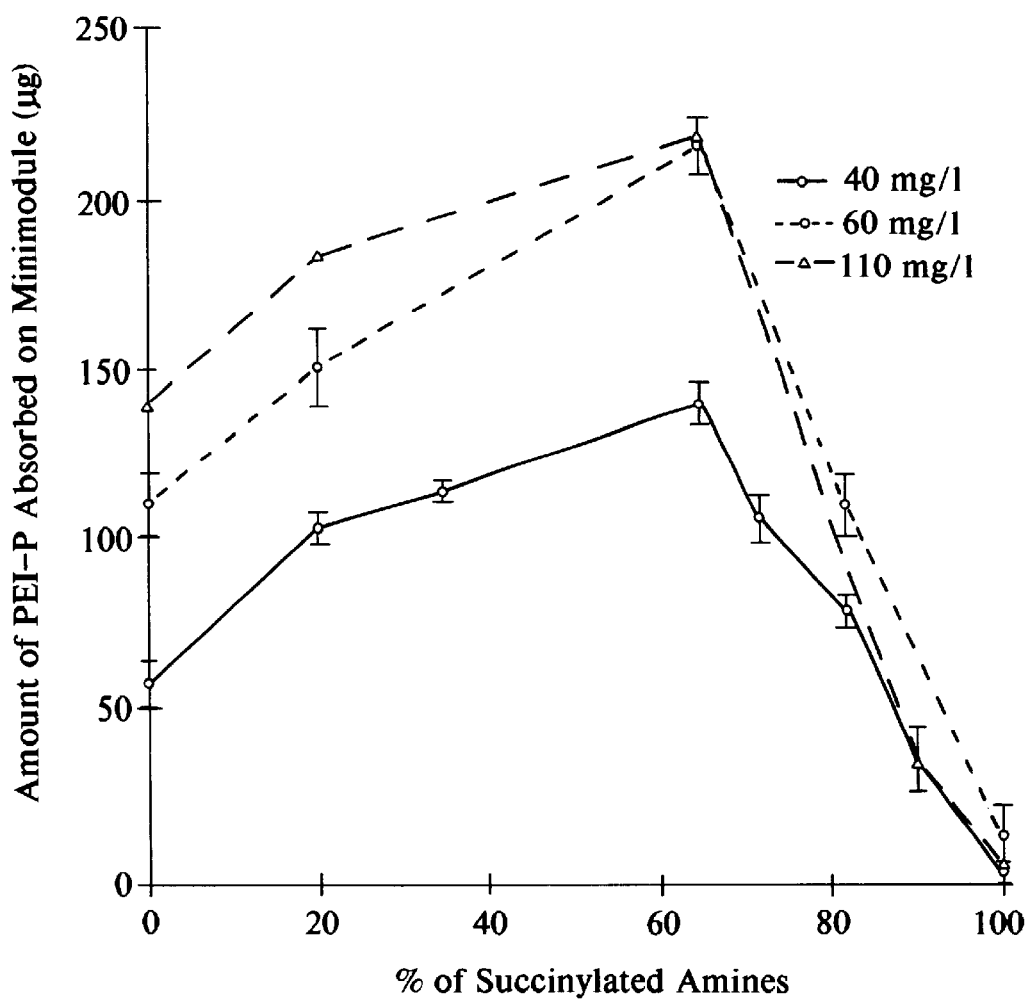

FIG. 20 shows the amount of pre-succinylated PEI-P per AN69 minimodule as a function of the degree of succinylation for different concentrations of pre-succinylated PEI-P.

Figure 21:
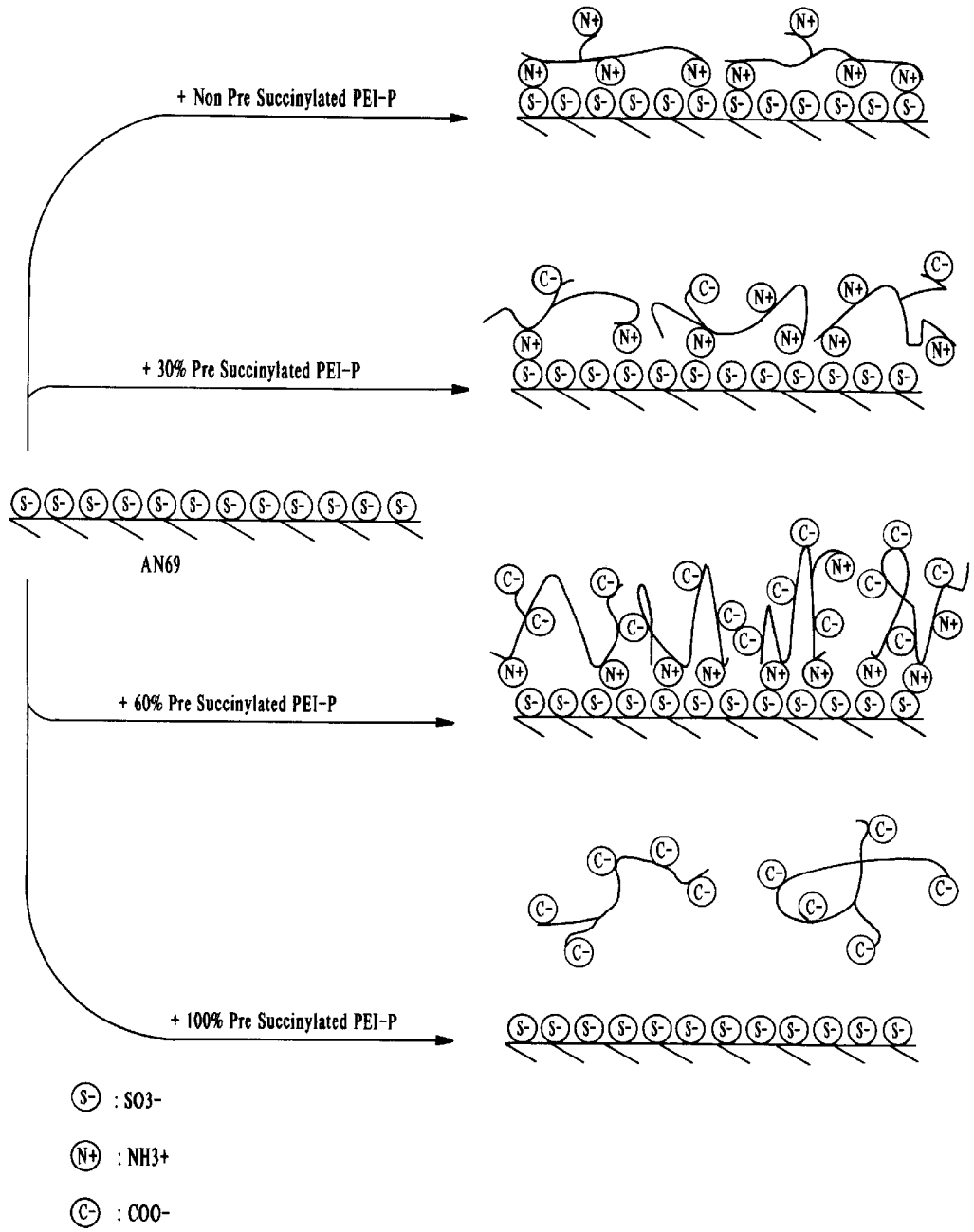

FIG. 21 is a schematic representation of the presentation of charged succinic acid groups explaining the results obtained depending on the degree of PEI-P pre-succinylation.

Figure 22:
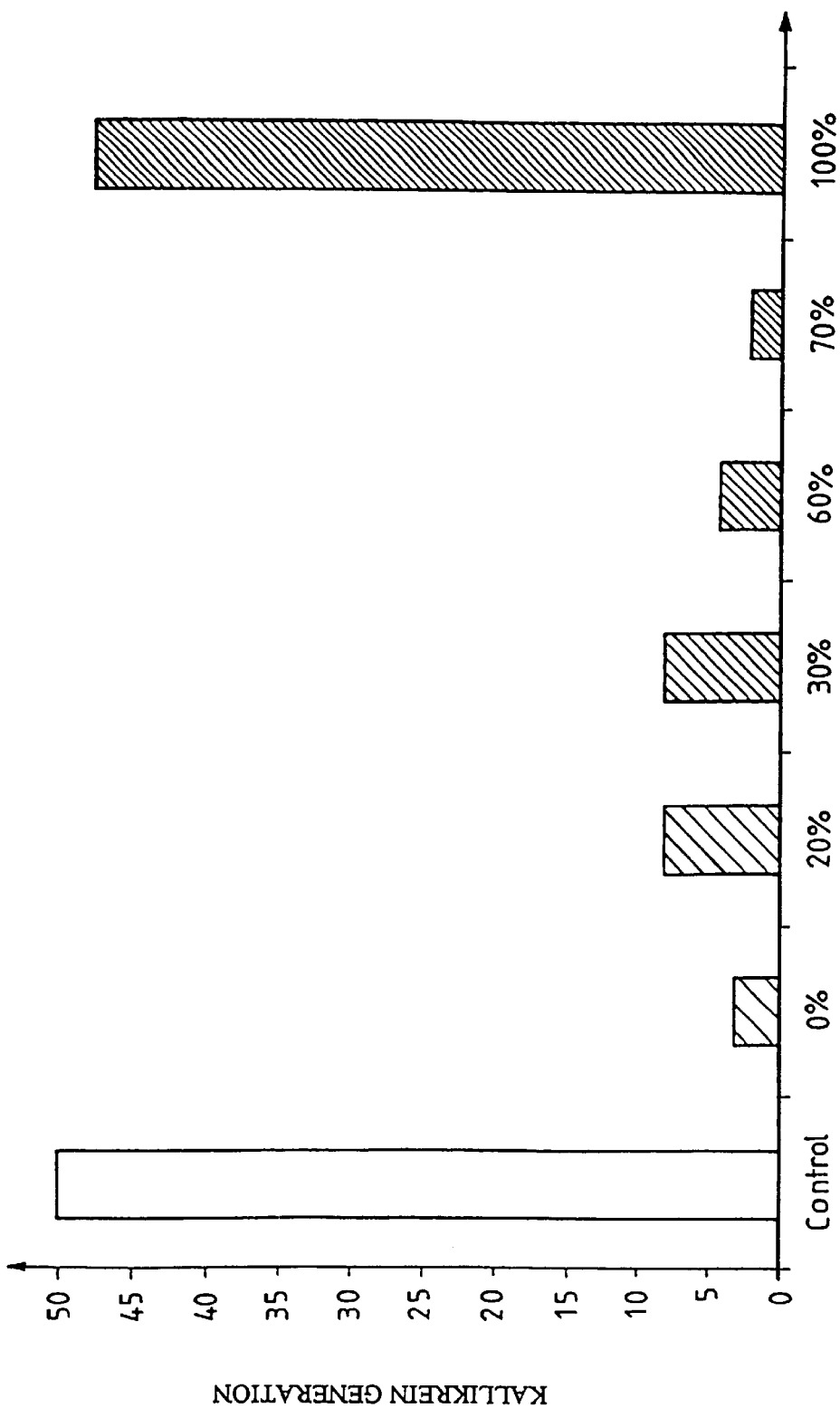

FIG. 22 shows the activation of the contact phase measured by the generation of kallikrein as a function of the degree of succinylation.

Figure 23:
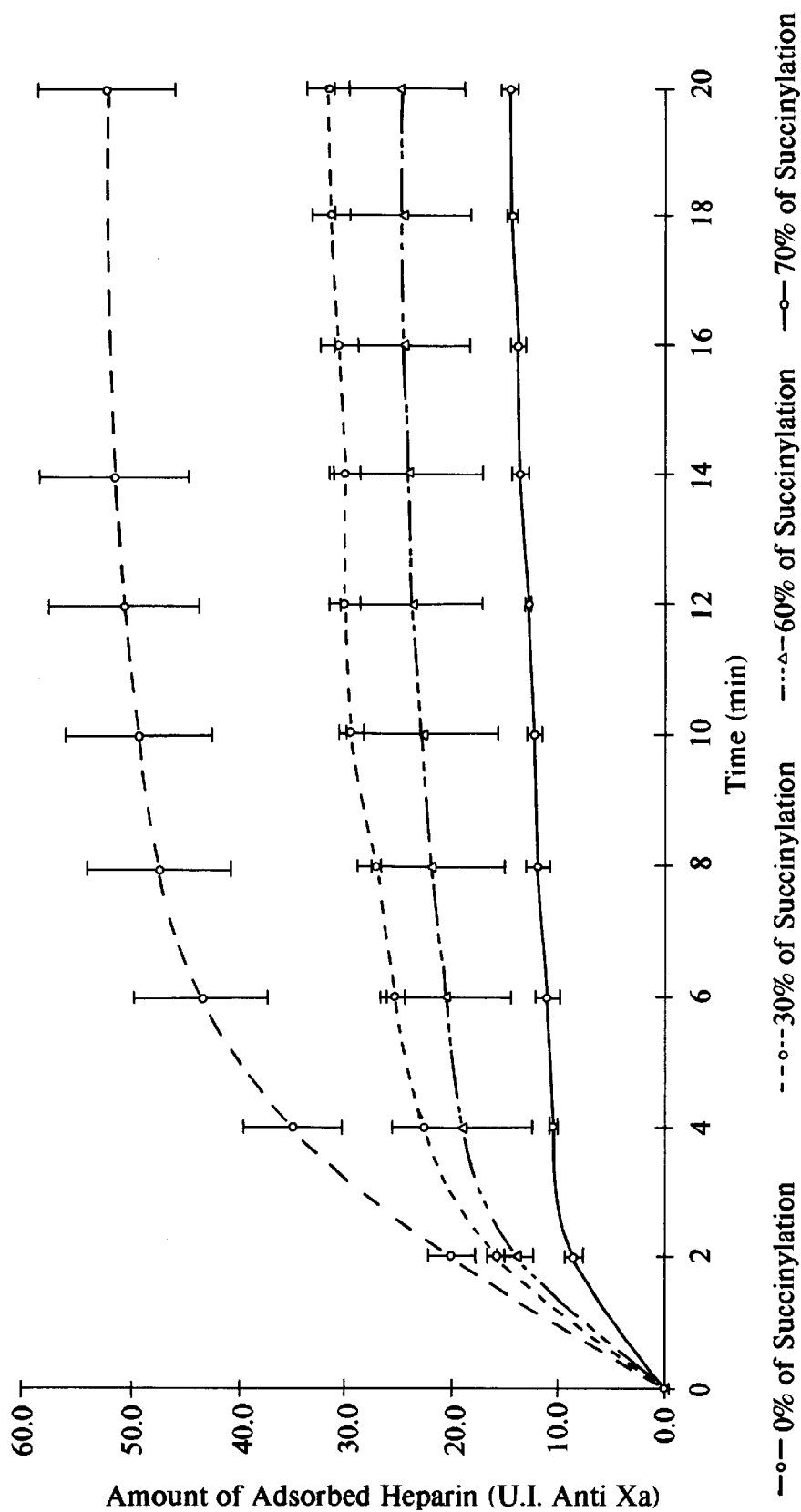

FIG. 23 indicates the amount of heparin which becomes bound on minimodules coated with pre-succinylated PEI-P as a function of the degree of pre-succinylation.

PROCESS FOR PREPARING FUNCTIONALIZED SUPPORTS

FOR SPECIFIC BIOLOGICAL PURIFICATION AND FOR DIALYSIS AND HEMOFILTRATION

The following study concerns the preparation of acrylonitrile copolymer type membranes treated by post-acylation or by pre-acylation. It shows the advantages of the second method for non specific biological purification applications (dialysis and/or hemofiltration membranes) or specific biological purification (coupling of one or more specific ligands for molecules to be eliminated).

The PEI modifications were carried out with the aim of:
- optimizing the degree of functionalisation, i.e., the number of reactive groups which can if necessary be coupled with a ligand;
- limiting the thrombogenicity observed with untreated polyanionic membranes while avoiding non specific binding, for example heparin binding.

The PEI used in these experiments was LUPASOL-P, sold by BASF with an average molecular weight of 750 000 daltons, measured by light diffusion.

Other types of PEI can be used, in particular Lupasol-WF sold by the same company, with an average molecular weight of 25 000.

The carboxylic acid anhydride used was succinic anhydride. The acylation in this case was succinylation.

1° Method

1.1 Surface Modification

All experiments were carried out using mini-dialysers comprising 170 hollow AN69 fibres (internal diameter: 210 μm; wall thickness: 42 μm; length: 0.18 m) and modified or non modified tritium-labelled PEI-P in solution in physiological serum (0.14 N NaCl). Two approaches were used:
a) the modules were first treated with tritium-labelled PEI-P then succinylated;
b) the modules were coated with tritium-labelled PEI-P which had already been completely or partially succinylated.

1.1 Preparation of PEI-P with Different Degrees of Succinylation:

Succinic anhydride (SA) dissolved in acetonitrile was added to 3 mg of PEI-P in 50 ml of 0.05 M borate, pH 8.6.

The following amounts of SA were added, depending on the degree of succinylation:

100% succinylation: 162 μmol of SA;
80% succinylation: 54 μmol of SA;
60% succinylation: 31 μmol of SA;
40% succinylation: 18 μmol of SA;
20% succinylation: 8 μmol of SA.

After a contact time of one hour with stirring and adjusting the pH to 8.6 if necessary with 0.1 M sodium hydroxide, the reaction was stopped by reducing the pH to 5 by adding 12 M acetic acid.

The degree of amine substitution was verified using fluorescamine using the method described in <<Pratique de l'analyse calorimetrique and fluorometrique>> [Calorimetric and Fluorometric Organic Analysis] by J. Bartos and M. Tesez, second edition, 1984, Masson, pages 84 to 85 (FIG. 17).

The pH was adjusted to 8 to coat the minimodules.

1.3 Evaluation of the Stability of the PEI Coated AN 69 Membrane

The stability of the surface modifications was evaluated by circulating a solution of NaCl at different concentrations (0.14 M, 1, 2 and 4 M).

1.4 Biological Evaluation

In order to evaluate whether the treated minimodules of the invention activated the contact phase, they underwent the following test: a biological liquid was prepared which could stimulate the production of kallikreins in contact with a membrane with a negative surface charge. The biological liquid used for the test was constituted by platelet depleted human plasma, diluted to 5% in physiological serum with added citrate (it should be noted that the test conditions used were far removed from the conditions for using the apparatus for extracorporeal blood circulation: the degree of dilution was very high, the liquid selected was plasma and not blood, and the plasma contained added citrate, and thus was acidified, while in dialysis, the anticoagulant used is heparin. These test conditions were deliberately chosen as they stimulated and amplified contact phase activation). 150 ml of this liquid was circulated in an open circuit in the blood compartment of a minimodule at a rate of 05 mil/min for 30 minutes.

Plasmatic kallikreins were assayed in liquid samples removed at intervals using a conventional chromogenic test with a S 2032 substrate from BIOGENIC.

Because of the sensitivity of the chromogenic test used, no significant increase in the number of kallikreins was considered to have occurred if the kallicrein concentration remained within about 10 units per liter.

2° Results Obtained 2.1 Surface Modification 2.1.2 Post-succinylation

The modules were firstly coated with tritium-labelled PEI-P then succinylated. The results are shown in Table I below:

TABLE I

Influence of post-succinylation on precipitation of PEI-P pre-adsorbed on AN69

| Quantity of PEI-P introduced onto AN69 (µg) | Quanitty of PEI-P retained on AN69 (µg) | Quantity of PEI-P remaining on AN69 after succinylation (µg) | Quantity of PEI-P precipitated after succinylation (µg) |
|---|---|---|---|
| 320 ± 12 | 57 ± 7 | 32 ± 2 | 25 ± 2 |

These results show that post-succinylation caused 43% of precipitation of PEI-P.

Further, the level of activation of the contact phase measured by the bias of kallikrein generation is shown in FIG. 18. This Figure compares the kallicrein produced, measured in units per liter, in the case of a naked AN69 membrane, a PEI-P coated AN69 membrane and an AN69 membrane coated with PEI-P then succinylated.

This figure shows that AN69 treated with PEI-P did not activate the contact phase. In contrast, since post-succinylation partially desorbs the PEI-P, AN69 treated with post-succinylated PEI-P activated the contact phase.

2.1.2 Effect of Pre-Succinylation

A minimodule coated with tritium-labelled PEI-P was pre-succinylated to various degrees (FIG. 17) and the quantity of pre-succinylated tritium-labelled PEI-P adsorbed on the AN69 was determined. The results are shown in FIG. 19.

FIG. 19 indicates that the quantity of PEI-P adsorbed on the AN69 increases with the degree of succinylation to reach a maximum at 60%. Above 60%, the quantity of adsorbed PEI-P reduces rapidly.

Further, the amount of adsorbed PEI-P increases both with the degree of succinylation (as shown in FIG. 19) and with the concentration of pre-succinylated PEI-P introduced into the minimodule. The maximum adsorption was observed with a PEI-P pre-succinylation of 60% in all cases.

FIG. 20 indicates that the amount of PEI-P adsorbed on the minimodule reached a plateau of 216 µg for concentrations of pre-succinylated PEI-P introduced into the minimodule of 60 mg/l or more.

2.1.3. Conclusion

The increase in adsorption of pre-succinylated PEI-P on AN69 modules can result from a conformational change resulting from a modification of electrostatic interactions between the charged amine and carboxy groups.

FIG. 21 is a schematic representation of the adsorption of non pre-succinylated PEI (top diagram) and 30%, 60% and 100% pre-succinylated PEI, onto an AN69 membrane.

When the PEI-P is not pre-succinylated, the number of amine groups per mole of PEI-P interacting with ionic groups ($SO_3^-$) of the membrane is large. Pre-succinylation reduces the number of amine groups per mole of PEI-P inducing a change in the conformation of the pre-succinylated PEI-P, which increases the amount of PEI-P adsorbed and as a result the number of available reactive sites for specific biological purification. Further, controlling the degree of pre-succinylation enables the quantity of reactive sites which can be obtained on thus treated AN69 membranes to be controlled.

In contrast, in the case of post-succinylation, it is clear from the first diagram of FIG. 21 that the number of reactive $N^+$ sites is relatively small, thus leading to a lower number of reactive carboxy sites after succinylation than in the case of pre-succinylation.

2.2 Stability of Non Succinylated and Pre-Succinylated Tritium-Labelled PEI after Washing Minimodules with Increasing Saline Concentrations For post-succinylation, coupling of succinic anhydride to PEI passes via a deprotonation step leading to precipitation of 30% to 40% of the PEI due to weakening of the bond between the $NH_3+$groups and the $SO_3^-$ groups of the membrane (as shown above in Table I).

Table II shows the percentage desorption of PEI-P after washing with increasing saline concentrations.

TABLE II

| SALINE CONCENTRATION DEGREE OF SUCCINYLATION | 0.14 M | 1 M | 2 M | 4 M |
|---|---|---|---|---|
| 0% | 0 | 0 | 13 | 13 |
| 20% | 0 | 0 | 16 | 16 |
| 60% | 0 | 0 | 42 | 54 |
| 90% | 0 | 0 | 49 | 71 |

The result shows that when the minimodules are treated with 40, 60 and 110 mg/l of pre-succinylated PEI-P then washed with 20 ml of physiological serum (0.14 M NaCl), there is no PEI-P desorption up to a saline concentration of 1 M. In contrast, when the minimodules are washed with a saline solution with a molarity of 2 M or more, partial desorption of pre-succinylated PEI-P is observed in all cases.

The level of pre-succinylated PEI-P desorption increases with the degree of pre-succinylation.

Treating minimodules with 60% pre-succinylated PEI-P is optimal for producing the maximum number of functional sites.

2.3 Hemocompatibility

FIG. 22 indicates that AN69 treated with 20% to 70% pre-succinylated PEI-P does not cause contact phase activation. In contrast, when the AN69 is treated with a 100% pre-succinylated PEI-P (FIG. 22), the contact phase activation observed is equivalent to that of AN69 not treated with PEI-P.

One supplemental advantage of treating the AN69 surface with pre-succinylated PEI-P is the reduction in heparin adsorption on the support with respect to the adsorption observed with AN69 treated with non succinylated PEI-P (FIG. 23). This represents a considerable advantage when these membranes are used for hemodialysis/hemofiltration as heparin is often used as an anticoagulant.

3° Conclusions

The comparative experiments have enabled the optimum conditions for preparing functionalised AN69 membranes to be prepared, in particular when they are treated with pre-acylated PEI-P. If the carboxylic acid anhydride is that of succinic acid, these conditions are as follows:
a degree of succinylation of 60%;
surface treatment at a concentration of 60 mg/l of pre-succinylated PEI.

This leads to:
a maximum functionality of 2 $\mu$M of COOH/m$^2$ of membrane;
a very good stability in a high ionic strength medium (up to 1 molar);
no blood contact phase activation;
limited heparin adsorption on the support which has a considerable advantage when this type of membranes is used in dialysis/hemofiltration.

In general, this technique enables the number of reactive sites present on the treated membrane to be controlled, namely:
the increase in the number of reactive sites for application to specific biological purification;
the reproducibility of the number of reactive sites obtained for all applications for the membranes of the invention.

The above experiments demonstrate the advantage of pre-succinylation over post-succinylation; in the latter, post-succinylation, precipitation of the pre-bound PEI causes probable formation of holes in the AN69 membrane coating. The existence of such holes leads to undesirable results, in particular contact phase activation observed on the naked, uncoated membrane.

EXAMPLE 1

Immobilisation of Anti IL6 Ab on Epoxided AN69 PEI-PEG

We performed experiments to determine the best method of immobilising anti IL6 Ab on insoluble supports, for example sepharose, and once that method had been found to apply it to AN69.

Two techniques for coupling Ab were carried out using tritium-labelled [$^3$H] IgG.
a) amide bond coupling to $\epsilon$NH$_2$ of lysine in the protein chain of the IgGs;
b) hydrazone bond coupling to oxidised carbohydrate groups which are found on the Fc portion of IgG using the technique described in the following documents: U.S. Pat. No. 4 217 338; Quash et al., J. Immunol. Methods, 1978 22, 15–175.

The sepharose beads and the anti IL6 Ab were brought into contact for 2 hours in increasing volumes of IL6 Ab deposited per volume of beads.

The quantity of radioactivity obtained for each sample of beads was then measured using a PACKARD MINAXI $\beta$ liquid scintillation counter.

The results are shown in Tables I and II below:

TABLE I

COVALENT COUPLING OF ANTI IL6 Ab ON SEPHAROSE BEADS

Bead support used (cm$^2$): 40

| I - A: VIA AMIDE BONDING | | | | |
|---|---|---|---|---|
| Quantity of non oxidised anti IL6 Ab introduced ($\mu$g) | 2.6 | 10 | 20 | 52 |
| Quantity of coupled non oxidised anti IL6 Ab ($\mu$g) | 0.54 | 2.64 | 5.20 | 13.60 |
| % of coupled non oxidised anti IL6 Ab | 21 | 26 | 26 | 26 |
| II - A: VIA HYDRAZONE BONDING | | | | |
| Quantity of oxidised anti IL6 Ab introduced ($\mu$g) | 2 | 8.4 | 16.8 | 42 |
| Quantity of coupled oxidised anti IL6 Ab ($\mu$g) | 0.38 | 2.72 | 6.26 | 18 |
| % of coupled oxidised anti IL6 Ab | 20 | 32 | 37 | 42 |

The results of Table I show that:
1) For low concentrations of anti IL6 Ab used, the quantity of coupled Ac represented 20% of the quantity of Ac deposited for both techniques (Table I);
2) Increasing the concentration of deposited anti IL6 Ab caused an increase in the quantity of coupled anti IL6 Ab in both techniques since it increased from 0.54 $\mu$g to 13.6 $\mu$g of coupled anti IL6 Ab for 40 cm$^2$ of beads when the anti IL6 Ab was coupled via an amide bond. This quantity was 0.38 $\mu$g to 18 $\mu$g of coupled anti IL6 Ab for 40 cm$^2$ of beads when the anti IL6 Ab was coupled via a hydrazone bond.
3) When the anti IL6 Ab were coupled via a hydrazone bond, the coupling yield increased as a function of the quantity of anti IL6 Ab deposited, passing from 20% to 42%, while for anti IL6 Ab coupled via an amide bond, the yield of coupled anti IL6 Ab remained constant (26%) as a function of the quantity of Ab deposited.

Experiments to determine the degree of adsorption of oxidised or non oxidised anti-IL6 antibodies on Sepharose beads showed that that adsorption did not exceed 7%.

It thus appears that while the quantity of coupled anti IL6 Ab increased for the two techniques as a function of the concentration of anti IL6 Ab deposited, the coupling efficiency of these anti IL6 antibodies is higher when these anti IL6 antibodies are coupled via a hydrazone bond.

This was more marked at high concentrations of added Ab:
42% for hydrazone bonding;
26% for amide bonding.

EXAMPLE 2

Immuno-Purification of IL6 Antigen on AN69 PEI-Epoxy PEG 2.1 On Sepharose Beads with Anti IL6 Ab Coupled via Amide or Hydrazone Bonding IL6 immuno-purification tests were carried out using:
beads on which anti IL6 Ab had been coupled in increasing quantities either via amide bonding or via hydrazone bonding using the techniques and ratios described in paragraph I, 1) and Table I;

and by varying the amount of IL6 present in the serums to be tested. To this end, we diluted a serum containing a very large quantity of IL6 (1.7 µg of IL6 per 1 ml of serum) in a mixture of previously tested negative serums. The serums tested then had a final IL6 amount of 33 050, 22 470, 11 235 and 3 157 pg/ml.

These sepharose/anti IL6 Ab beads were then brought into contact with different mixtures of modified serums in proportions of a volume of beads per volume of serums.

The amount of IL6 in the serums before and after passage was measured by a sandwich type immunoenzymatic technique.

The results are shown in Table II below.

TABLE IIa

% immuno-purified IL6 after passage over beads:
VIA AMIDE BONDING

| Quantity of coupled non oxidised anti IL6 Ab ($\mu$g/40 cm$^2$) | Quantity of IL6 introduced (pg/ml) | % IL6 retained |
|---|---|---|
| 0.54 | 3157 | 86.9 |
| | 11235 | 75.7 |
| | 22470 | 67.6 |
| | 35050 | 18.5 |
| 2.64 | 3157 | 97.9 |
| | 11235 | 89.6 |
| | 22470 | 93.9 |
| | 35050 | 81.3 |
| 13.6 | 3157 | 98.1 |
| | 11235 | 98.9 |
| | 22470 | 1 |
| | 35050 | 97.8 |

TABLE IIb

% immuno-purified IL6 after passage over beads:
VIA HYDRAZONE BONDING

| Quantity of coupled non oxidised anti IL6 Ab ($\mu$g/40 cm$^2$) | Quantity of IL6 introduced (pg/ml) | % IL6 retained |
|---|---|---|
| 0.38 | 3157 | 57 |
| | 11235 | |
| | 22470 | 41.7 |
| | 35050 | 28.5 |
| 2.72 | 3157 | 89.1 |
| | 11235 | 72.5 |
| | 22470 | 70.9 |
| | 35050 | 54.2 |
| 18.00 | 3157 | 99.3 |
| | 11235 | 97.4 |
| | 22470 | 98.7 |
| | 35050 | 90.0 |

These results shown that:
1) the support alone (beads without anti IL6 Ab), treated or not treated with hydrazine, did not bind IL6;
2) the higher the quantity of coupled anti IL6 Ab, the more effective the IL6 immuno-purification for both coupling techniques used;
3) when the anti IL6 Ab was coupled in an amount of 13.6 µg/40 cm$^2$ (amide bonding) and 18 µg/40 cm$^2$ (hydrazone bonding), IL6 immuno-purification was 90–100% effective for the two coupling techniques used and for serums containing a low or high amount of IL6.
4) for quantities of coupled anti IL6 Ab of less than 13.6 µg/40 cm$^2$ (amide bonding) and 18 µg/40 cm$^2$ (hydrazone bonding), IL6 immuno-purification reduced as a function of the quantity of coupled anti IL6 Ab and as a function of the amount of IL6 present in the serum.

When anti IL6 Ab was coupled via amide bonding at 2.64 µg/40 cm$^2$, the immuno-purification efficiency reduced from 98% for a serum with 3.157 pg/ml of IL6 to 81.3% for a serum with 35 030 pg/ml of IL6. Similarly, when the anti IL6 Ab was coupled at 0.54 µg/40 cm$^2$, the immuno-purification efficiency reduced from 86.9% for a serum with 3 157 pg/ml of IL6 to 18.5% for a serum with 35 030 pg/ml (Table II).

When the anti IL6 Ab was coupled via hydrazone bonding at 2.72 µg/40 cm$^2$, the immuno-purification efficiency reduced from 89.1% for a serum with 3 157 pg/ml of IL6 to 54.2% for a serum with 35 030 pg/ml of IL6. Similarly, when the anti IL6 Ab was coupled at 0.38 µg/40 cm$^2$, the immuno-purification efficiency reduced from 57.1% for a serum with 3 157 pg/ml of IL6 to 28.5% for a serum with 35 030 pg/ml (Table III).

Conclusion

Coupling of anti IL6 Ab via an amide bond or via a hydrazone bond conserves their activity as regards IL6.

In order for immuno-purification of IL6 present in a serum containing up to 35 000 pg/ml to be 90-100% effective, the quantity of coupled anti IL6 Ab must be of the order of 0.4 µg/cm$^2$. This immuno-purification efficiency is the same for anti IL6 Ab coupled either via amide bonding or via hydrazone bonding.

For quantities of coupled anti IL6 Ab of less than 0.4 µg/cm$^2$, the IL6 immuno-purification efficiency falls as theQuantity of IL6 in the serum increases. This is true for both bonding types, however when the anti IL6 Ab are coupled via amide bonding, IL6 immuno-purification is generally more effective than when the anti IL6 antibodies are coupled via hydrazone bonding.

The optimum quantity of coupled anti IL6 Ab per cm$^2$ for complete IL6 immuno-purification having been defined for beads, we could then move on to IL6 immuno-purification on AN69 minimodules.

2.2 IL6 Immuno-Purification Tests on AN69 Minimodules

Minimodules were hydrophilised and functionalised (H & F) using the method described in WO 92/07023.

1) Methods

Minimodules comprising 170 hollow fibres of AN69 18 cm long were assembled (internal surface area: 256 cm 2). These minimodules were treated with PEG tetraepoxide to generate epoxide groups.

We coupled $^3$H propionate labelled anti IL6 Ab via hydrazone bonding to one of the AN69 minimodules under the same conditions as for 0.4 µg/cm$^2$ of beads, knowing that these 0.4 µg/cm$^2$ of coupled Ab theoretically represented 42% of the Ab deposited if it was assumed that the coupling efficiency of AN69 fibres was similar to the coupling efficiency on sepharose beads.

Thus we brought 0.95 µg of Ab per cm$^2$ of fibre into contact, i.e., 243 µg of Ab for 256 cm$^2$ of fibres.

Further, we coupled control goat Ab, still via hydrazone bonding, to the second AN69 minimodule under the same conditions as for the AN69+anti IL6 Ab minimodule.

Three ml of 11 203 pg/ml IL6 serum was recycled over two hours through these minimodules (0.5 ml/mn).

Then the amount of IL6 present was measured using a sandwich type immunoenzymatic technique before and after passage through the minimodules.

According to Table III, it appears the immuno-purification was effective and specific since after passage over AN69 grafted with control Ac only 14% of the IL6 was removed non specifically while after passage over AN69 with anti IL6 Ab the degree of immuno-purification increased to 77.5%.

TABLE III

IMMUNO-PURIFICATION OF IL6 AFTER PASSAGE OVER AN69:

|  | IL6 before passage over AN69 | IL6 after passage over AN69 + oxidised Ab controls | IL6 after passage over AN69 + oxidised anti IL6 Ab |
| --- | --- | --- | --- |
| pg/ml | 11203 | 9623 | 2512 |
| Immuno-purified IL6 % | 0 | 14.0 | 77.5 |

Under the experimental conditions used, the degree of binding of anti-IL6 2 antibody on the AN69 module was 0.11 µg/cm$^2$.

The most likely hypothesis which can explain this medium amount of coupling of anti IL6 Ab on AN69 fibres is the scarcity of epoxide sites on the fibre surface and thus the scarcity after treatment with adipic dihydrazide of hydrazine groups available to generate a hydrazone bond with the aldehydes of the carbohydrate portion of the oxidised Ac.

We know that IL6 immuno-purification is 100% effective for serums with an IL6 content of <35 000 pg/ml, provided that the quantity of coupled anti IL6 Ab is at least 0.4 µg/cm$^2$. We now have at our disposal a system (AN69 fibre) which probably will not allow such a density of covalently coupled Ab per cm$^2$ to be obtained and thus limits IL6 immuno-purification.

2.3 Control of the Capacity to Bind the Complement

The seric IL6 purification efficiency using the hydrophilised and functionalised (H & F) AN69 minimodule grafted with anti IL6 Ab having been proved, we determined whether this chemically modified minimodule would retain its initial property as regards non reactivity towards the complement. Thus we verified its capacity to bind or not to bind the complement.

H & F AN69 membranes did not bind the complement adjusted to 0.625 HU50 or to 2.5 HU.

H & F AN69 cartridges grafted with Ab specifically eliminated the corresponding antigen and did not cause complement binding.

EXAMPLE 3

Preparation of Post-Succinylated AN69 PEI for Specific Biological Purification

This preparation was carried out by treating minimodules with PEI WF followed by post-succinylation.

3.1 Determination of the Number of Available Sites on AN69-PEI for Binding Low Molecular Weight (LMW) Molecules 2) After Functionalisation of AN69-PEI by Succinic Anhydride For this study, we used a module constituted by a flat membrane with a surface area of 1 m$^2$. This module had been treated with PEI then dismantled to enable 4.5 cm$^2$ samples of the membrane to be removed from the ends and the centre of the module using a punch.

We compared the number of available sites on these AN69-PEI pellets with reference AN69 control using a radio-labelled LMW molecule: [$^{14}$C] ethanolamine.

Succinic anhydride was then bound using the following protocol:

a 1 M solution of succinic anhydride in acetonitrile was prepared;

this was diluted to ¹⁄₁₀ in 50 mM borate buffer at pH 8.5, leaving it in contact with the control AN69 pellets and AN69 PEI for 15 minutes;

Carrying out the operation a second time;

Intensive H$_2$O washes were carried out.

The labelled ethanolamine had bound to the portions obtained as follows:

a) activation of COOH groups generated:
a-1) a solution of 3-ethyl(3-dimethylaminopropylcarbodiimide) (EDC) (50 nM) and N-hydroxysuccinimide (NHS) (50 nM) in 10 nM NaH$_2$PO$_4$ was prepared and left in contact with the pellets for 15 minutes.

a-2) the activation solution was eliminated.

b) Ethanolamine binding:
b-1) Isotopic normal ethanolamine/labelled ethanol amine dilutions 4 nmol normal/0.4 nmol labelled;
40 nmol normal/0.4 nmol labelled;
400 nmol normal/0.4 nmol labelled;
4000 nmol normal/0.4 nmol labelled;

Each solution being prepared in 50 mM borate, final pH 8.

b-2) Left in contact with control AN69 pellets and AN69-PEI pellets for two hours with stirring, then washed with 0.5 M borate/NaCl and counted.

FIG. 6 shows that:

the optimal quantity of ethanolamine retained on AN69+PEI+succinic anhydride was 5.6 nmol/pellet;

the quantity of ethanolamine retained on AN69+succinic anhydride was 1.2 nmol/pellet.

Thus the quantity of ethanolamine actually retained on AN69+succinylated PEI was 5.6−1.2=4.4 nmol/4.5 cm$^2$, i.e.: 1 nmol/cm$^2$ or 10 µmol/m$^2$.

Finally, FIG. 6 shows that the quantity of ethanolamine retained on AN69+succinylated PEI was homogeneous over the whole of the module since we found the same number of sites at the module inlet, centre and outlet.

2) After functionalisation of AN69 succinylated PEI using adipic dihydrazide (ADH).

The ADH was bound as follows:

After activation of the COOH groups (see a)), a 50 mM solution of ADH in 50 mM borate, pH 8.5 was prepared and left in contact with AN69 pellets for 1 hour.

It was washed with a large quantity of borate then H$_2$O then acetate.

Binding of $^{14}$C pyruvic acid on the pellets was carried out as follows:

Isotopic normal ethanolamine/labelled ethanolamine dilutions in 1 ml of 50 nM acetate, pH 5.4 were prepared:

0 nmol normal/5 nmol labelled;
20 nmol normal/5 nmol labelled;
200 nmol normal/5 nmol labelled;
2000 nmol normal/5 nmol labelled;

They were left in contact for two hours, then washed with acetate, 0.5 M NaCl and count.

FIG. 7 shows that the optimal quantity of pyruvic acid retained on AN69+ADH was 0.1 nmol/pellet with or without activation (EDC) of the support.

FIG. 8 shows that the optimal quantity of pyruvic acid retained on succinylated AN69+ADH was 0.5 nmol/pellet with or without activation (EDC) of the support for quantities of pyruvic acid introduced of over 150 nmol per pellet.

FIG. 9 shows that:

the quantity of coupled pyruvic acid on AN69+PEI +succinic anhydride+ADH was at least 1.1 nmol per pellet after activation of the carboxy groups generated on the support (via succinic anhydride) for binding via the amide bond of ADH;

when the carboxy groups generated on the support were not activated, the quantity of pyruvic acid adsorbed on AN69+PEI+succinylation+ADH was 0.45 nmol per pellet.

In conclusion, functionalization of AN69 by PEI firstly and then by succinic anhydride increases the number of sites available for low molecular weight molecules at least five-fold. This increase is of the same order of magnitude after treatment with ADH.

3.2 Determination of the Number of Available Sites on AN69-PEI for Binding High Molecular Weight (HMW) Molecules For this study, we brought two oxidised or non oxidised concentrations (5 $\mu$g and 60 $\mu$g) of immunoglobulin (Ig) into contact with functionalized or non functionalized AN69 pellets.

| | $\mu$g of non oxidised Ig retained | | $\mu$g of oxidised Ig retained | |
|---|---|---|---|---|
| $\mu$g of Ig introduced | on AN69 | on AN69 + PEI + ADH | on AN69 | On AN69 + PEI + ADH |
| 5 | 0.122 | 0.290 | 0.452 | 0.870 |
| 60 | 0.950 | 2.835 | 3.990 | 7.760 |

Functionalisation of AN69 firstly by PEI and then by succinic anhydride and finally by ADH enabled the number of available sites for high molecular weight molecules to be at least doubled.

EXAMPLE 4

Figure 1:
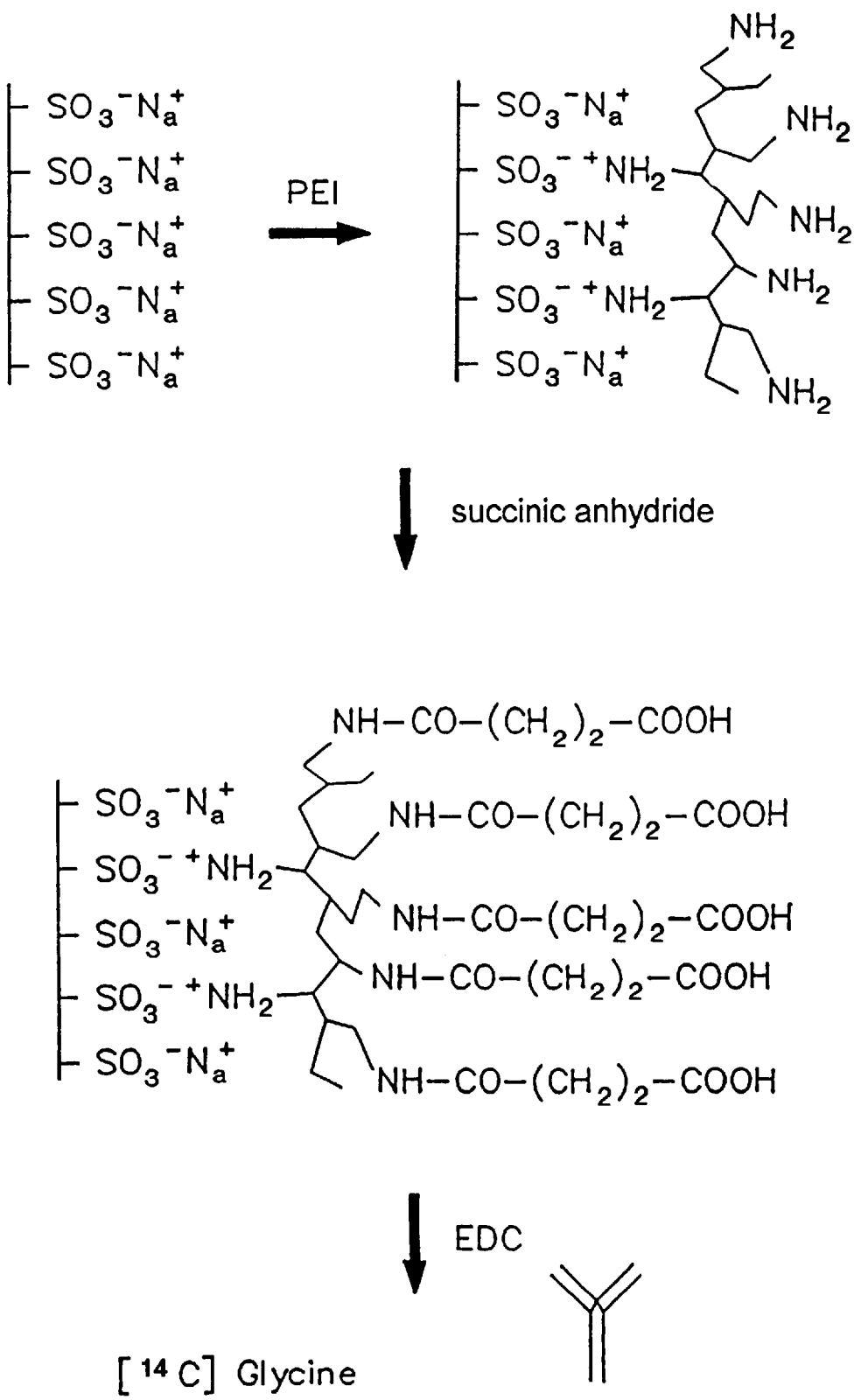
FIG. 1 is an illustration of the coupling of a low molecular weight molecule, glycine, or an antibody, to a PEI functionalized support with succinylated amine groups.
Figure 2:
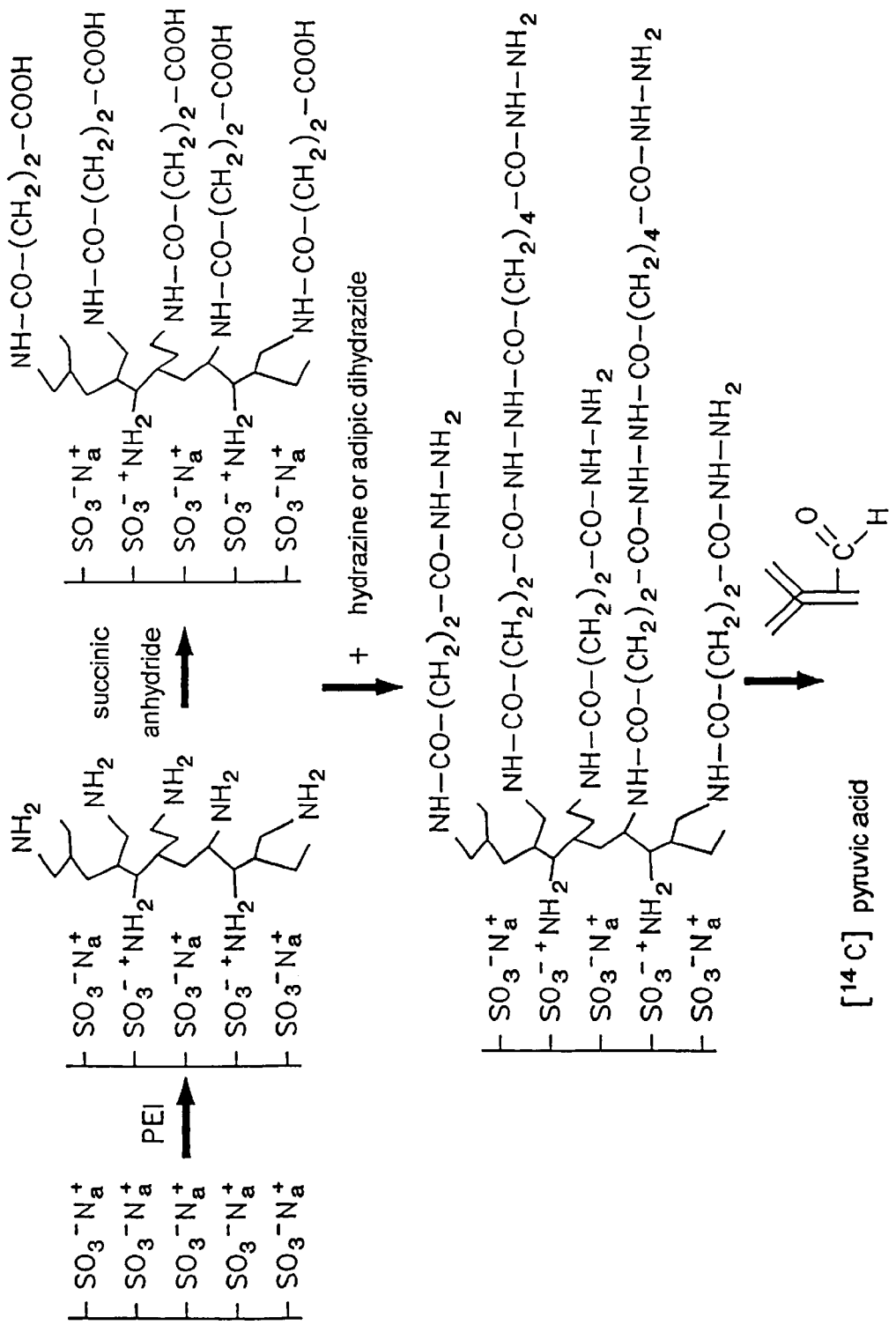
FIG. 2 shows a similar coupling via hydrazone bonding to a low molecular weight molecule (pyruvate) or a high molecular weight molecule (oxidized antibody).
Figure 3:
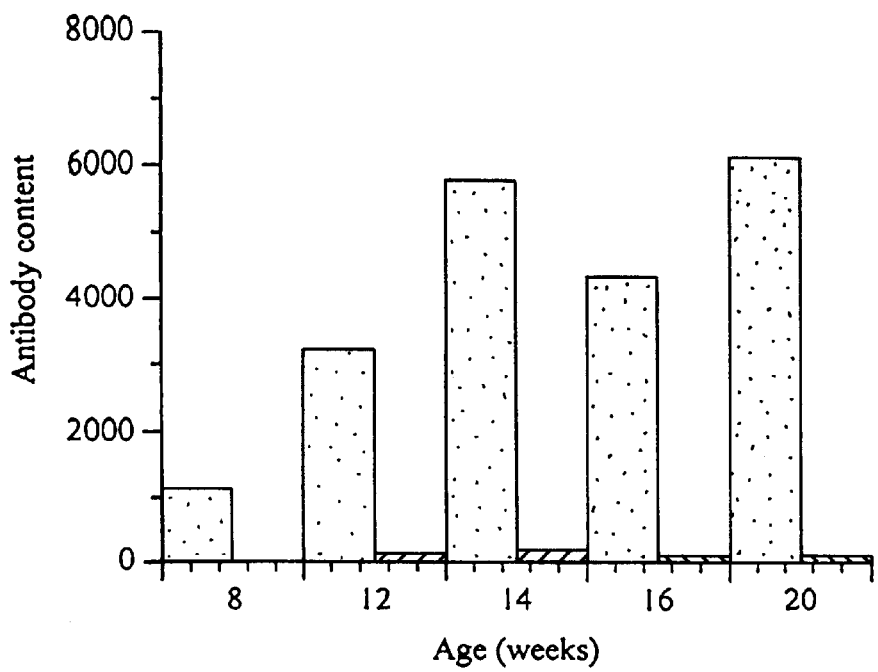
FIG. 3 shows the anti-lipoic acid antibody content in the serum of the MLR mouse. The light grey shows the content in MLR/lpr mice and the dark hatched grey shows the amount obtained with MLR/mp mice.
Figure 4:
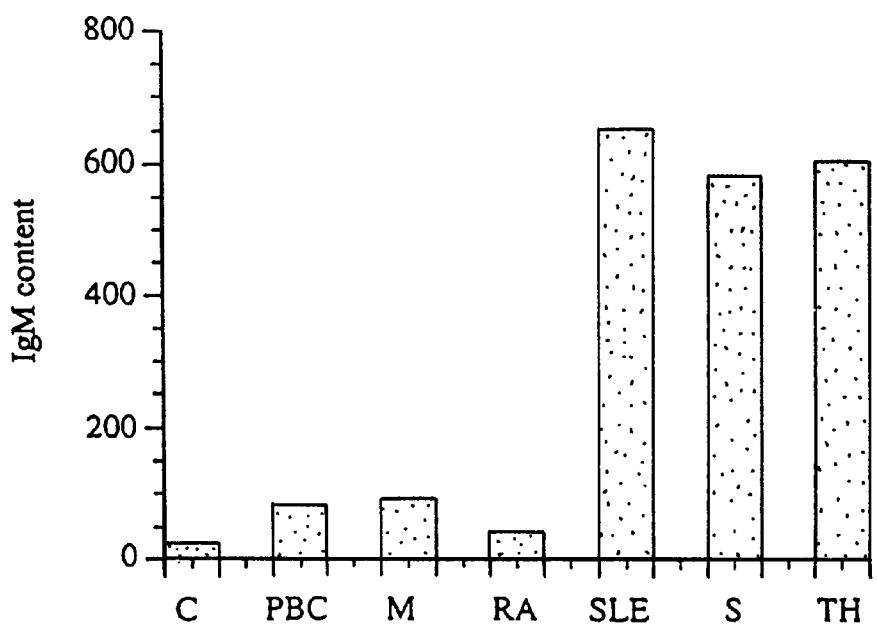
FIG. 4 shows a comparison of the amount of anti-lipoic acid IgM for different pathologies. C represents the control, PBC represents primary biliary cirrhosis, M represents myasthenia, RA represents rheumatoid arthritis, SLE represents systemic lupus erythematosus, S represents syphilis and TH represents thyroiditis.

Immuno-Purification of Anti-Lipoic Acid (LA) Antibodies on Post-Succinylated AN69 PEI Regarding SLE, the results shown in FIGS. 1, 2 and 3 urged us to develop cartridges which could specifically eliminate anti LA Ab from the plasma of patients with SLE. The LA was a haptene with a MW of 100 kDa, the technique developed could be extended to other haptenes containing functional COOH groups.

Covalent binding of LA on an insoluble support was carried out as follows:

the terminal epoxy functional group was directly substituted with putrescein to form an arm ending in an α NH$_2$ onto which lipoic acid had been grafted by an amide bond (see FIG. 1).

Figure 5:
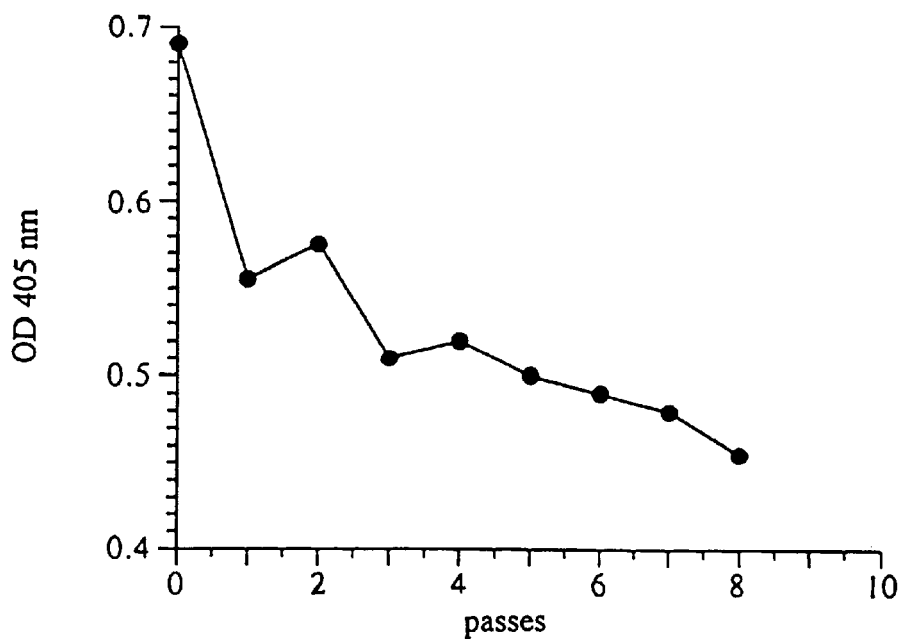
FIG. 5 shows the reduction in anti-DNA antibodies eliminated after passing a lupus serum over a support which is covalently coupled to lipoic acid.

This was necessary for two reasons: firstly, it should enable re-use of the cartridge after elution of the antibodies in an alkaline medium and secondly, the amide bond is intrinsically far more stable than the ester bond (see FIG. 2) which would have been formed if LA had been directly coupled with the OH groups of the hydrolysed epoxide (see FIG. 5).

4.1 Comparative Study of Immuno-Purification as a Function of the Type of LA Bonding FIG. 5 shows that immuno-purification of anti-LA IgM was much more effective when the LA was coupled via an amide bond since all of these anti-LA was eliminated while LA coupled via an ester bond only caused a slight reduction in anti-LA IgM, of the order of 8%.

The immuno-purification efficiency of anti-LA Ab by LA coupled via an amide bond being proved, the following step consisted of testing re-use and thus the stability of the support.

We thus immuno-purified six samples from the same lupic serum.

4.2 AN69 H & F—LA Minimodule Re-use Tests

FIG. 8 shows that six successive passages with an elution step between each passage over the same support of six different samples originating from the same lupic serum resulted in identical anti-LA purification efficiency for the first through to the sixth passage..

Successive elution of retained proteins after these six passages gave the same profile on a polyacrylamide gel (FIG. 9).

Conclusion

We have thus developed on AN69 an effective anti-LA Ab immuno-purification system which is specific and re-usable for extracorporeal circulation.

EXAMPLE 5

Covalent Coupling of Purified IgG on Pre-Succinylated AN69-PEI-P:

5.1 Apparatus

The experiments were carried out using minidialysers comprising 170 hollow fibres of AN69 (internal diameter: 210 $\mu$m; wall thickness: 42 $\mu$m; length: 0.18 m).

Goat IgG was from Biosys (Compiègne, France).

Mouse IgG and rabbit IgG were laboratory purified on a protein A sepharose column from a pool of ascites liquid and on a DEAE cellulose from rabbit serum respectively.

5.2 Method

5.2.3 Preparation of Radio-Labelled IgG

Mouse, rabbit and goat IgG were radiolabelled with N-succinidyl (2–3$^3$H) propionate and the excess radioactivity was eliminated by dialysis.

Specific activity of IgG after dialysis:

mouse IgG: 1.25×10$^6$ cpm/mg protein;

rabbit IgG: 1.86×10$^6$ cpm/mg protein;

goat IgG: 0.77×10$^6$ cpm/mg protein.

5.2.2 Modification of Minimodules 5.2.2.3) 6 minimodules were deglycerined then treated with a 60% pre-succinylated PEI-P solution;

5.2.2.4) 3 minimodules, A, B, C, were then activated by a carbodiimide while the other 3, D, E, F, were left as they were;

5.2.2.5) 50 $\mu$g of radiolabelled rabbit IgG was recycled for 2 hours in PBS (final volume: 3 ml) over minimodules A and D.

50 μg of radiolabelled mouse IgG was recycled for 2 hours in PBS (final volume: 3 ml) over minimodules B and E.

50 μg of radiolabelled goat IgG was recycled for 2 hours in PBS (final volume: 3 ml) over minimodules C and F.

5.2.2.4) The 6 minimodules were then washed until there were no more traces of radioactivity.

The quantity of coupled IgG corresponded to the quantity of radioactivity introduced—the quantity of radioactivity recovered.

| 5.3 Results: Quantity of IgG coupled to pre-succinylated AN69 | | |
|---|---|---|
| Support | Quantity of IgG introduced (μg) | Quantity of IgG reained |
| A | 50 | 3.74 |
| B | 50 | 7.82 |
| C | 50 | 3.80 |
| D | 50 | 7.05 |
| E | 50 | 3.60 |
| F | 50 | 6.30 |

What is claimed is:

1. A module for extracorporeal purification of a biological fluid, said module comprising at least one compartment for circulating said biological fluid, wherein said at least one compartment is delimited by an ionic functionalized support or an ionic functionalized wall, a surface of said support or wall being bonded to a first molecule by ionic bonds which exhibits free amine groups to which are covalently bonded a second molecule which exhibits free carboxylic groups which can directly or indirectly form amide, ester or thioester bonds.

2. The module according to claim 1, comprising a surface which further comprises a third molecule which is bonded by covalent bonding to said carboxylic groups, wherein said third molecule acts as a spacer to reduce steric hindrance and enhances the binding of a ligand, a molecule or elements to be purified.

3. The module according to claim 2, wherein said surface further comprises a fourth molecule which is bonded by covalent bonding to said carboxylic groups and increases the hydrophilic nature of said surface to limit non-specific interactions.

4. The module according to claim 3, wherein said surface further comprises a fifth molecule which is covalently bonded to said carboxylic groups and covalently couples a ligand carrying the groups —CHO or —COOH.

5. The module according to any one of claims 2 to 4, wherein said third, fourth and fifth molecules are a dihydrazide having the formula:

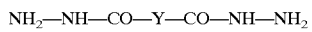

where Y is a $(CH_2)_m$ group and wherein m is 2 to 6.

6. The module according to claim 1, wherein the support comprises a membrane which is a semi-permeable membrane produced from a copolymer of acrylonitrile and sodium methallyl sulphonate.

7. The module according to claim 1, wherein said first molecule or macromolecule is a substituted or non-substituted polyethyleneimine (PEI) with a molecular weight of 10,000 to 2,000,000 daltons.

8. The module according to claim 1, wherein said second molecule is a dicarboxylic acid anhydride having the formula:

where X is $(CH_2)_n$ and n is 2 or 3 or X is —CH=CH—.

9. The module according to claim 1, wherein said second molecule is a monocarboxylic acid anhydride having the formula:

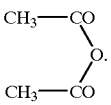

10. A kit comprising:
 a multipurpose module of claim 1 or claim 2;
 a sterile pouch or receptacle containing a solution of a selected ligand;
 a sterile pouch or receptacle containing an activating solution; and
 buffer or rinsing solutions for activation and/or covalent coupling of a ligand.

11. The kit according to claim 10 wherein said activating solution is carbodiimide and the ligand is lipoic acid.

12. The kit according to claim 10, wherein the activating solution is sodium periodate and the ligand is an antibody.

13. A process for preparing a functionalized biocompatible support carrying groups which form covalent bonds with organic groups, said process comprising the steps of:
 (a) bringing a support comprising bound anionic groups into contact with a substituted or non-substituted polyethyleneimine (PEI) having a molecular weight of 10,000 to 2,000,000 daltons to form a treated support;
 (b) bringing said treated support of (a) into contact with a solution of a dicarboxylic acid anhydride having the formula:

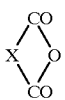

where X is $(CH_2)_n$ and wherein n is equal to 2 or 3 or X is —CH=CH—, or with a monocarboxylic acid anhydride having the formula:

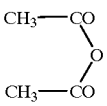

to form a functionalized biocompatible support.

14. The process according to claim 13 further comprising the step of bringing the support modified by steps (a) and (b) into contact with a dihydrazide having the formula:

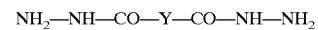

wherein Y is a $(CH_2)_m$ group where m is from 2 to 6.

15. A process for preparing a functionalized biocompatible support carrying groups which form covalent bonds with organic groups, said process comprising the steps of:
 (a) reacting a substituted or non-substituted polyethyleneimine (PEI) having a molecular weight of 10,000 to 2,000,000 daltons with a solution of a dicarboxylic acid anhydride having the formula:

where X is $[CH_2]_n$ and wherein n is 1 to 4, or X is —CH=CH—, or a monocarboxylic acid anhydride having the formula:

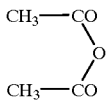

to form a reaction mixture; and (b) bringing said support into contact with said reaction mixture to form a functionalized biocompatible support.

16. The process according to claim 15, wherein said organic groups are:

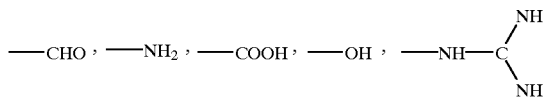

17. The process according to claim 15, further comprising the step of bringing said functionalized biocompatible support into contact with a dihydrazide having the formula:

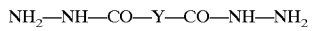

wherein Y is a $[CH_2]_m$ group and m is 2 to 6.

18. The process according to claim 17, wherein the dihydrazide is adipic dihydrazide.

19. The process according to claim 15, wherein said support is an ionic support.

20. The process according to claim 19, wherein said ionic support is a copolymer of acrylonitrile and sodium methallyl sulphonate.

21. The process of claim 5, wherein said carboxylic acid anhydride is succinic anhydride.

22. A functionalized biocompatible support obtained by the process of claim 13 or claim 15.

23. The support according to claim 22, wherein said support is covalently coupled to a ligand.

24. The support according to claim 23, wherein said ligand is selected from the group consisting of antibodies, antigens, peptides, proteins, glycoproteins, hormones, enzymes, cofactors, substrates, inhibitors, polysaccharides, lectins, toxins, antitoxins, nucleic acids, polynucleotides, haptenes, pigments, stains, and combinations thereof.

25. The support according to claim 22, wherein said support is part of a membrane.

26. The support according to claim 25, wherein said membrane is in the form of porous or non-porous flat films solid or hollow fibers porous or non-porous microbeads or a combination thereof.

27. The support according to claim 26, wherein said membrane is a dialysis membrane.

28. A module for extracorporeal purification of a biological fluid, said module comprising at least one compartment for circulating said biological fluid, wherein said at least one compartment is delimited by an ionic functionalized support or an ionic functionalized wall, a surface of said support or wall being bonded to (1) a first molecule by ionic bonds which exhibits free amine groups to which are covalently bonded (2) a second molecule, which exhibits free carboxylic groups, which can directly or indirectly form amide, ester, or thioester bonds; and (3) a third molecule, which is a dihydrazide having the formula:

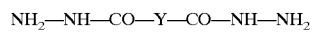

where Y is a $(CH_2)_m$ group and wherein m is 2 to 6.

29. The module according to claim 28, wherein said surface further comprises a fourth molecule and a fifth molecule, each of which is a dihydrazide having the formula:

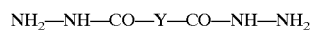

where Y is a $(CH_2)_m$ group and wherein m is 2 to 6.

30. A process for preparing a functionalized biocompatible support carrying groups, which form covalent bonds with organic groups, said process comprising the steps of:

(a) bringing a support composing bound anionic groups into contact with a substituted or non-substituted polyethyleneimine (PEI) having a molecular weight of 10,000 to 2,000,000 daltons to form a treated support;

(b) bringing said treated support of (a) into contact with a solution of a dicarboxylic acid anhydride having the formula:

where X is $(CH_2)_n$ and wherein n is equal to 2 or 3 or X is —CH=CH—, or with a monocarboxylic acid anhydride having the formula:

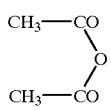

to form a functionalized biocompatible support; and (c) bringing the functionalized biocompatible support modified by steps (a) and (b) into contact with a dihydrazide having the formula:

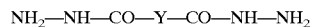

wherein Y is a $(CH_2)_m$ group where m is from 2 to 6.

31. A process for preparing a functionalized biocompatible support carrying groups, which form covalent bonds with organic groups, said process comprising the steps of:

(a) reacting a substituted or non-substituted polyethyleneimine (PEI) having a molecular weight of 10,000 to 2,000,000 daltons with a solution of a dicarboxylic acid anhydride having the formula:

where X is $[CH_2]_n$ and wherein n is 1 to 4, or X is —CH=CH—, or a monocarboxylic acid anhydride having the formula:

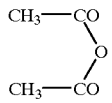

to form a reaction mixture;
(b) bringing said support into contact with said reaction mixture to form functionalized biocompatible support, and
(c) bringing said functionalized biocompatible support into contact with a dihydrazide having the formula:

wherein Y is a $(CH_2)_m$ group where m is from 2 to 6.

32. A functionalized biocompatible support comprising:
(a) a copolymer of acrylonitrile and sodium methallyl sulphonate to which is bonded to the surface of said copolymer:
  (i) a first molecule, which is a substituted or non-substituted polyethyleneimine (PEI), wherein said first molecule or macromolecule is ionically bonded and exhibits free amine groups;
  (ii) a second molecule, which is a dicarboxylic acid anhydride having the formula:

where X is $(CH_2)_n$ and n is 2 or 3 or X is —CH=CH— or with a monocarboxylic acid anhydride having the formula:

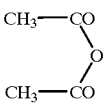

to form a functionalized biocompatible support,
wherein said second molecule is covalently bonded to said free amine groups and wherein said second molecule exhibits free carboxylic groups, which can directly or indirectly form amide, ester or thioester bonds; and
  (iii) a third molecule, which is covalently bonded to said carboxlic groups of said second molecule and is a dihydrazide having the formula:

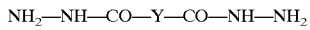

wherein Y is a $(CH_2)_m$ group where m is from 2 to 6.

33. The module according to claim 32, wherein said surface further comprises a fourth molecule and a fifth molecule, each of which is a dihydrazide having the formula:

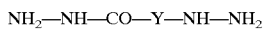

where Y is a $(CH_2)_m$ group and wherein m is 2 to 6.

* * * * *

UNITED STATES PATENT AND TRADEMARK OFFICE
CERTIFICATE OF CORRECTION

PATENT NO.    : 6,260,715 B1
DATED         : July 17, 2001
INVENTOR(S)   : Simard et al.

It is certified that error appears in the above-identified patent and that said Letters Patent is hereby corrected as shown below:

Column 26,
Line 13, in the formula, change "O." to -- O --;

Column 27,
Line 46, change "claim 5" to -- claim 15 --;
Line 61, change "films" to -- films, --.

Signed and Sealed this

Eleventh Day of June, 2002

Attest:

JAMES E. ROGAN
Attesting Officer    Director of the United States Patent and Trademark Office